US011554182B2

(12) United States Patent
Wilson et al.

(10) Patent No.: US 11,554,182 B2
(45) Date of Patent: Jan. 17, 2023

(54) MACROCYCLIC COMPLEXES OF ALPHA-EMITTING RADIONUCLIDES AND THEIR USE IN TARGETED RADIOTHERAPY OF CANCER

(71) Applicant: CORNELL UNIVERSITY, Ithaca, NY (US)

(72) Inventors: Justin Wilson, Ithaca, NY (US); Nikki Thiele, Kingston, TN (US)

(73) Assignee: Cornell University, Ithaca, NY (US)

( * ) Notice: Subject to any disclaimer, the term of this patent is extended or adjusted under 35 U.S.C. 154(b) by 10 days.

(21) Appl. No.: 16/499,070

(22) PCT Filed: Mar. 30, 2018

(86) PCT No.: PCT/US2018/025488
§ 371 (c)(1),
(2) Date: Sep. 27, 2019

(87) PCT Pub. No.: WO2018/183906
PCT Pub. Date: Oct. 4, 2018

(65) Prior Publication Data
US 2021/0085808 A1 Mar. 25, 2021

Related U.S. Application Data

(60) Provisional application No. 62/478,945, filed on Mar. 30, 2017.

(51) Int. Cl.
| A61K 51/00 | (2006.01) |
| A61M 36/14 | (2006.01) |
| A61K 51/04 | (2006.01) |
| A61K 51/10 | (2006.01) |
| A61P 35/00 | (2006.01) |

(52) U.S. Cl.
CPC ...... *A61K 51/0482* (2013.01); *A61K 51/1051* (2013.01); *A61K 51/1096* (2013.01); *A61K 2121/00* (2013.01); *A61P 35/00* (2018.01)

(58) Field of Classification Search
CPC ............ A61K 51/0482; A61K 51/1051; A61K 51/1096; A61K 2121/00; A61P 35/00
See application file for complete search history.

(56) References Cited

U.S. PATENT DOCUMENTS

| 4,597,903 A | 7/1986 | Gokel et al. |
| 5,747,345 A | 5/1998 | Weber, II et al. |
| 10,806,806 B2 * | 10/2020 | Babich ............... A61K 51/0482 |
| 2010/0081799 A1 | 4/2010 | Knor et al. |

FOREIGN PATENT DOCUMENTS

| CN | 103421133 | * 12/2013 |
| JP | 200298981 A | * 4/2002 |
| WO | WO 2015/176056 A1 | 11/2015 |
| WO | WO 2016/096843 A1 | 6/2016 |

OTHER PUBLICATIONS

Tsukube et al. (J. Org. Chem. 1992, 57, 542-547).*
Bordunov et al. (Tetrahedron 1997, 53, 17595-17606).*
Ver Heyen et al. (Tetrahedron 1999, 55, 5207-5226).*
Barrett, et al., "First-in-Man Evaluation of 2 High-Affinity PSMA-Avid Small Molecules for Imaging Prostate Cancer," J. Nucl. Med. 2013, 54, 380.
Beyer, et al., Comparison of the Biodistribution of $^{225}$Ac and Radio-Lanthanides as Citrate Complexes, Isot. Environ. Heal. Stud., vol. 26, 111-114 (1990).
Chamas, et al., "Clicked dipicolinic antennae for lanthanide luminescent probes," Dalton Trans., vol. 39, pp. 7091-7097 (2010).
Corson, et al., "Efficient Multigram Synthesis of the Bifunctional Chelating Agent (S)-1-p-Isothiocyanatobenzyl-diethylenetetraminepentaacetic Acid," Bioconjug. Chem., vol. 11, pp. 292-299 (2000).
Crawford, et al., "$^{211}$Rn/$^{211}$At and $^{209}$At production with intense mass separated Fr ion beams for preclinical $^{211}$At-based a-therapy research," Appl. Radiat. Isot., vol. 122, pp. 222-228 (2017).
Davis, K. A. Glowienka, R. A. Boll, K. A. Deal, M. W. Brechbiel, M. Stabin, P. N. Bochsler, S. Mirzadeh, S. J. Kennel, Nucl. Med. Biol. 1999, 26, 581.
Deal, I. A. Davis, S. Mirzadeh, S. J. Kennel, M. W. Brechbiel, J. Med. Chem. 1999, 42, 2988.
Dennis, M. Zhang, Y. Gloria Meng, M. Kadkhodayan, D. Kirchhofer, D. Combs, L. A. Damico, J. Biol. Chem. 2002, 277, 35035.
Dolomanov, et al., "OLEX2: a Complete Structure Solution, Refinement and Analysis Program," J. Appl. Crystallogr., vol. 42, pp. 339-341 (2009).
Dumelin, et al., "A Portable Albumin Binder form a DNA-Encoded Chemical Library," Angew. Chem. Int. Ed., 47, 3196-3201 (2008).
Ferreirós-Martínez, D. Esteban-Gómez, É. Tóth, A. de Blas, C. Platas-Iglesias, T. Rodríguez-Blas, Inorg. Chem. 2011, 50, 3772.
Ferrier, et al., "Synthesis and Characterization of the Actinium Aquo Ion," ACS Cent. Sci., vol. 3, 176-185 (2017).

(Continued)

*Primary Examiner* — Michael G. Hartley
*Assistant Examiner* — Melissa J Perreira
(74) *Attorney, Agent, or Firm* — Foley & Lardner LLP

(57) ABSTRACT

The present technology provides compounds as well as compositions including such compounds useful for the treatment of cancers where the compounds are represented by the following formula (I) or a pharmaceutically acceptable salt thereof, wherein M is an alpha-emitting radionuclide.

(I)

16 Claims, 4 Drawing Sheets

(56) References Cited

OTHER PUBLICATIONS

Ferrier, et al., "Spectroscopic and computational investigation of actinium coordination chemistry," Nat. Commun. 2016, 7, 12312 (2016), 8 pages.
Gatto, et al., "Synthesis of Calcium-Selective, Substituted Diaza-Crown Ethers: A Novel, One-Step Formation of Bibracchial Lariat Ethers (BiBLEs)," J. Am. Chem. Soc., vol. 106, 8240-8244 (1984).
Ghosh, et al., "Tumor Target Prostate Specific Membrane Antigen (PSMA) and Its Regulation in Prostate Cancer," J. Cell. Biochem., vol. 91, pp. 528-539 (Feb. 2004).
Hillier, et al., "Preclinical Evaluation of Novel Glutamate-Urea-Lysine Analogues That Target Prostate-Specific Membrane Antigen as Molecular Imaging Pharmaceuticals for Prostate Cancer," Cancer Res., vol. 69, pp. 6932-6940 (2009).
Jensen, "Aqueous Complexes for Efficient Size-based Separation of Americium from Curium," Inorg. Chem., vol. 53, pp. 6003-6012 (2014).
Kelly, Synthesis and pre-clinical evaluation of a new class of high-affinity 18F-labeled PSMA ligands for detection of prostate cancer by PET imagingA. Amor-Coarasa, A. Nikolopoulou, D. Kim, C. Williams, S. Ponnala, J. W. Babich, Eur. J. Nucl. Med. Mol. Imaging 2017, 44, 647-661.
Kozikowski, F. Nan, P. Conti, J. Zhang, E. Ramadan, T. Bzdega, B. Wroblewska, J. H. Neale, S. Pshenichkin, J. T. Wroblewski, J. Med. Chem. 2001, 44, 298.
Leveque, L. Gigou, J. P. Bergerat, Curr. Clin. Pharmacol. 2008, 3, 51.
Leyland-Jones, et al., Pharmacokinetics, safety, and efficacy of trastuzumab administered every three weeks in combination with paclitaxel, J. Clin. Oncol., vol. 21, pp. 3965-3971 (Sep. 2003).
Maresca, et al., A Series of Halogenated Heterodimeric Inhibitors of Prostate Specific Membrane Antigen (PSMA) as Radiolabeled Probes for Targeting Prostate Cancer J. Med. Chem., vol. 52(2), pp. 347-357 (2009).
Mato-Iglesias, et al., Lanthanide Complexes Based on a 1,7-Diaza-12-crown-4 Platform Containing Picolinate Pendants: A New Structural Entry for the Design of Magnetic Resonance Imaging Contrast Agents, Inorg. Chem., vol. 47, pp. 7840-7851 (Aug. 2008).
McDevitt, et al., "Tumor Therapy with Targeted Atomic Nanogenerators," *Science*, vol. 294, 1537-1540 (Nov. 2001).
Miranda-Hernández, et al., "Theoretical approximations and experimental extinction coefficients of biopharmaceuticals," Anal. Bioanal. Chem., vol. 408, pp. 1523-1530 (2016).
Moasser, "The oncogene HER2: its signaling and transforming functions and its role in human cancer pathogenesis," Oncogene 2007, 26, 6469.
Müller, "Practice suggestions for better crystal structures," Crystallogr. Rev. 2009, 15, 57-83.
Neil, M. A. Fox, R. Pal, L.-O. Palsson, B. A. O'Sullivan, D. Parker, Dalton Trans. 2015, 44, 14937-14951.
Price, K. J. Edwards, K. E. Carnazza, S. D. Carlin, B. M. Zeglis, M. J. Adam, C. Orvig, J. S. Lewis, Nucl. Med. Biol. 2016, 43, 566-576.
Radchenko, et al., "Application of ion exchange and extraction chromatography to the separation of actinium from proton-irradiated thorium metal for analytical purposes," J. Chromatogr. A, vol. 1380, pp. 55-63 (2015).
Sheldrick, "A short history of SHELX," Acta Crystallogr. Sect. A, vol. 64, pp. 112-122 (2008).
Sheldrick, "SHELXT—Integrated space-group and crystal-structure determination," Acta Crystallogr. Sect. A, vol. 71, pp. 3-8 (2015).
Zielinska, et al., "An Improved Method for the Production of Ac-225/Bi-213 from TH-229 for Targeted Alpha Therapy," Solvent Extr. And Ion Exch., vol. 25, pp. 339-349 (2007).
Search Report issued in co-pending European Patent Application No. 18775715.8, dated Oct. 16, 2020.
Price, et al., "Matching chelators to radiometals for radiopharmaceuticals", Chemical Society Reviews, vol. 43, No. 1, pp. 260-290, (Oct. 2013).
Wilson, et al., "Evaluation of nitrogen-rich macrocyclic ligands 1 chelation of therapeutic bismuth radioisotopes", Nuclear Medicine and Biology., vol. 42, No. 5, pp. 428-438 (May 2015).
Wilbur, "Chemical and radiochemical considerations in radiolabeling v [alpha]-emitting radionuclides", Current Radiopharmaceuticals, Bentham Science Publishers Ltd., NL, vol. 4, No. 3, pp. 214-247 (Jul. 2011).
Roca-Sabio et al., "Macrocyclic Receptor Exhibiting Unprecedented Selectivity for Light Lanthanides," *Journ. Of the American Chem. Society*, vol. 131, pp. 3331-3341 (2009).
Thiele et al., "An Eighteen-Membered Macrocyclic Ligand for Actinium-225 Targeted Alpha Therapy," *Angew. Chem. Int. Ed.*, vol. 56, pp. 14712-14717 (2017).
Notice of Reasons for Rejection issued in co-pending Japanese Patent Application No. 2019-553433, dated Jan. 11, 2022.
Tsukube, et al., "Pyridino-armed diaza-crown ethers for specific transport of transition metal cations", Tetrahedron Letters, vol. 29, issue 5, pp. 569-572 (1988).
Jensen, et al., "Aqueous Complexes for Efficient Size-based Separation of Americium from Curium," *American Chemical Society*, vol. 53, pp. 6003-6012 (2014).
Filing Receipt and Application Data Sheet from U.S. Appl. No. 62/353,735.
Certified Priority document for U.S. Appl. No. 62/478,945.

\* cited by examiner

Side View

Top View

MACROCYCLIC COMPLEXES OF ALPHA-EMITTING RADIONUCLIDES AND THEIR USE IN TARGETED RADIOTHERAPY OF CANCER

CROSS-REFERENCE TO RELATED APPLICATIONS

This application is a U.S. national phase application under 35 U.S.C. § 371 of International Application No. PCT/US2018/025488, filed on Mar. 30, 2018, which claims the benefit of and priority to U.S. Provisional Patent Application No. 62/478,945, filed on Mar. 30, 2017, the entire disclosure of which is incorporated herein by reference for any and all purposes.

U.S. GOVERNMENT LICENSE RIGHTS

This invention was made with Government support under grant number UL1TR00457 awarded by the National Institutes of Health. The Government has certain rights in the invention.

FIELD

The present technology generally relates to macrocyclic complexes of alpha-emitting radionuclides, as well as compositions including such compounds and methods of use.

SUMMARY

In an aspect, a composition of Formula I is provided

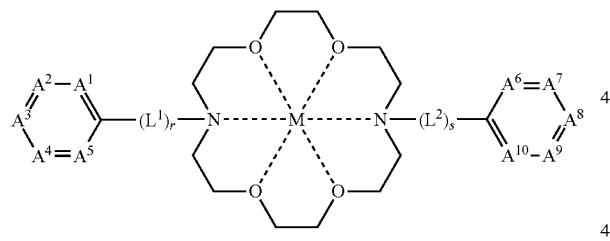

(I)

or a pharmaceutically acceptable salt thereof, where M is an alpha-emitting radionuclide, $A^1$ represents a nitrogen atom (N) or $CR^1$; $A^2$ represents a nitrogen atom (N) or $CR^2$; $A^3$ represents a nitrogen atom (N) or $CR^3$; $A^4$ represents a nitrogen atom (N) or $CR^4$; $A^5$ represents a nitrogen atom (N) or $CR^5$; $A^6$ represents a nitrogen atom (N) or $CR^6$; $A^7$ represents a nitrogen atom (N) or $CR^7$; $A^8$ represents a nitrogen atom (N) or $CR^8$; $A^9$ represents a nitrogen atom (N) or $CR^9$; and $A^{10}$ represents a nitrogen atom (N) or $CR^{10}$; provided that no more than three of $A^1$, $A^2$, $A^3$, $A^4$, and $A^5$ can be nitrogen atoms, and no more than three of $A^6$, $A^7$, $A^8$, $A^9$, and $A^{10}$ can be nitrogen atoms; $R^1$, $R^2$, $R^3$, $R^4$, $R^5$, $R^6$, $R^7$, $R^8$, $R^9$, and $R^{10}$ are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —(OCH$_2$CH$_2$)$_x$—R', —(OCH$_2$CH$_2$)$_y$—OR', —OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3; or one or two pairs of directly adjacent $R^1$, $R^2$, $R^3$, $R^4$, $R^5$, $R^6$, $R^7$, $R^8$, $R^9$, and $R^{10}$ groups are interconnected to form a five- to six-membered substituted or unsubstituted carbocyclic or nitrogen-containing ring; where R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl, or wherein two R' groups attached to the same atom are interconnected to form a three- to six-membered ring.

The groups $L^1$ and $L^2$ in Formula (I) are linkers independently selected from —(CH$_2$)$_p$—, where p is a value of 1, 2, or 3. The subscripts r and s in Formula (I) are independently 0 or 1. When r is 0 or when s is 0, then $L^1$ or $L^2$, respectively, is not present, which results in a direct bond between the respective aromatic ring and the macrocycle.

In an aspect, a targeting composition is provided that is represented by Formula (II)

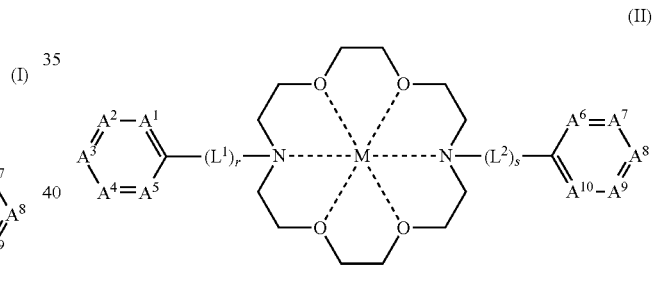

(II)

In Formula (II), $A^1$-$A^{10}$, M, $L^1$, $L^2$, r, and s have the same meanings provided for any embodiment herein with the exception that at least one of $R^1$-$R^{10}$ is or includes a selective cancer cell targeting group.

In another aspect, methods of producing a composition according to Formula (I) and/or Formula (II) are provided.

In another aspect, the present technology also provides compositions (e.g., pharmaceutical compositions) and medicaments comprising any of one of the embodiments of the compounds of Formula II (or a pharmaceutically acceptable salt thereof) disclosed herein and a pharmaceutically acceptable carrier or one or more excipients or fillers.

In another aspect, the present technology provides a method of treating cancer by administering an effective amount of the targeting composition according to Formula (II) to a subject having cancer.

BRIEF DESCRIPTION OF THE DRAWINGS

FIG. 1D, top view). Ellipsoids are drawn at the 50% probability level. Counteranions and hydrogen atoms attached to carbons are omitted for clarity.

FIGS. 2A-C shows the biodistribution of $^{225}$Ac(NO$_3$)$_3$ (FIG. 2A), [$^{225}$Ac(macropa)]$^+$ (FIG. 2B), and [$^{225}$Ac(DOTA)]$^-$ (FIG. 2C) for select organs following intravenous injection in mice. Adult C57BL/6 mice were sacrificed 15 min, 1 h, or 5 h post injection. Values for each time point are given as mean % ID/g±1 SD.

DETAILED DESCRIPTION

Figure 1A:
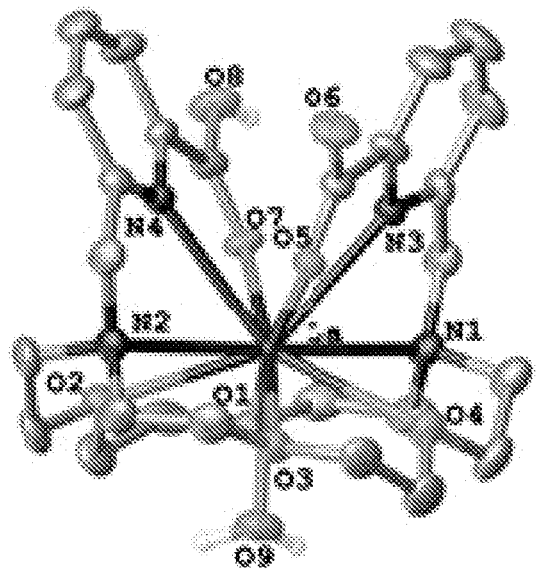
FIGS. 1A and 1B shows x-ray crystal structures of [La(Hmacropa)(H$_2$O)].(ClO$_4$)$_2$ (FIG. 1A, side view.
Figure 1B:
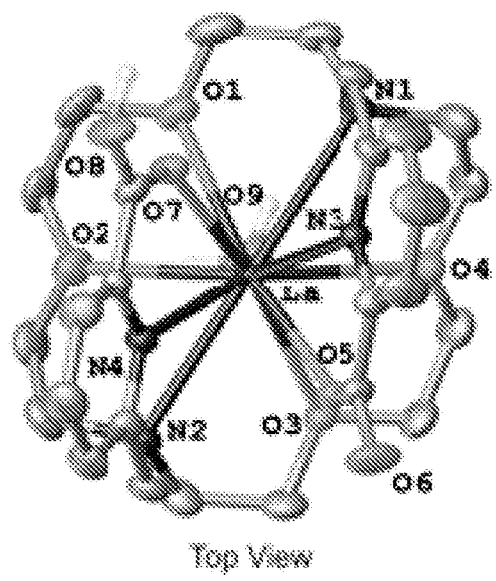
Figure 1C:
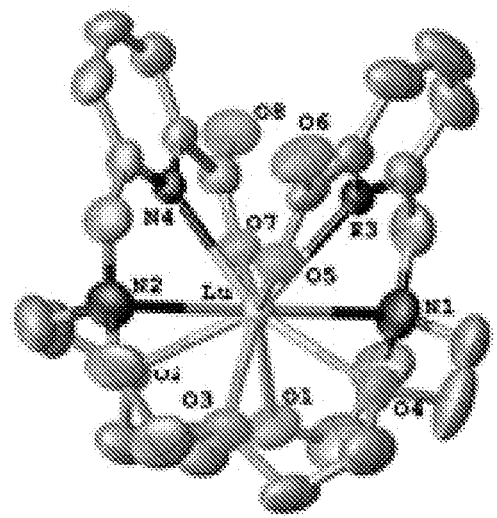
FIGS. 1C and 1D shows x-ray crystal structures of [Lu(macropa)].ClO$_4$.DMF (FIG. 1C, side view.
Figure 1D:
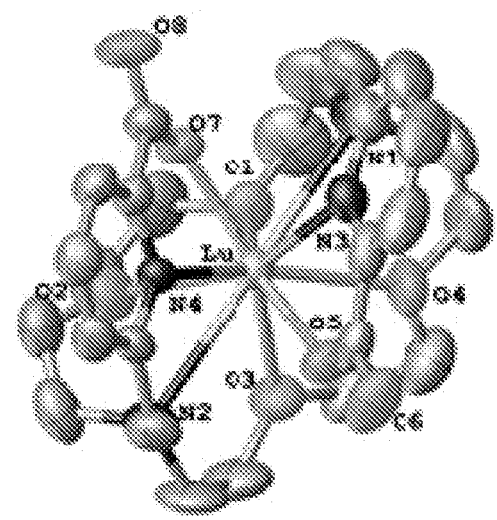

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., SF$_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O$^-$ group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

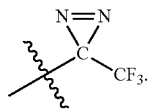

The term "isocyano" refers to —NC.
The term "isothiocyano" refers to —NCS.
The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

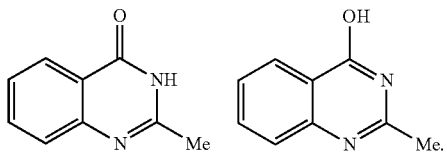

As another example, guanidines may exhibit the following isomeric forms in protic organic solution, also referred to as tautomers of each other:

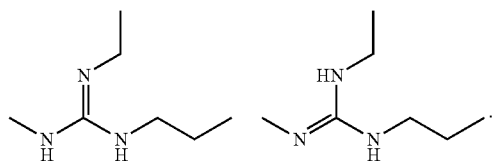

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the present technology.

The Present Technology

Although targeted radiotherapy has been practiced for some time using macrocyclic complexes of radionuclides, the macrocycles currently in use (e.g., DOTA) generally form complexes of insufficient stability with radionuclides, particularly for radionuclides of larger size, such as actinium, radium, bismuth, and lead isotopes. Such instability results in dissociation of the radionuclide from the macrocycle, and this results in a lack of selectivity to targeted tissue, which also results in toxicity to non-targeted tissue.

The present technology provides new macrocyclic complexes that are substantially more stable than those of the conventional art. Thus, these new complexes can advantageously target cancer cells more effectively, with substantially less toxicity to non-targeted tissue than complexes of the art. Moreover, the new complexes can advantageously be produced at room temperature, in contrast to DOTA-type complexes, which generally require elevated temperatures (e.g., at least 80° C.) for complexation with the radionuclide. The present technology also specifically employs alpha-emitting radionuclides instead of beta radionuclides. Alpha-emitting radionuclides are of much higher energy, and thus substantially more potent, than beta-emitting radionuclides.

Thus, in one aspect, a composition of Formula I is provided:

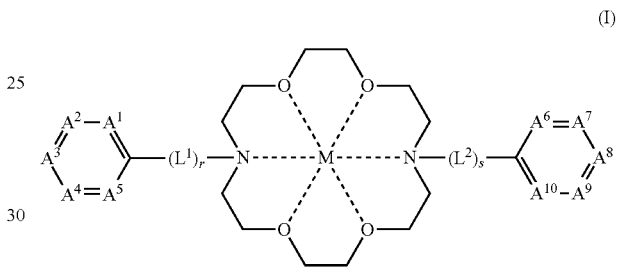

or a pharmaceutically acceptable salt thereof, where M is an alpha-emitting radionuclide. Exemplary alpha-emitting radionuclides include, but are not limited to, actinium-225 ($^{225}Ac^{3+}$), radium-223 ($^{233}Ra^{2+}$), bismuth-213 ($^{213}Bi^{3+}$) lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), and uranium-230.

In Formula I, $A^1$ represents a nitrogen atom (N) or $CR^1$; $A^2$ represents a nitrogen atom (N) or $CR^2$; $A^3$ represents a nitrogen atom (N) or $CR^3$; $A^4$ represents a nitrogen atom (N) or $CR^4$; $A^5$ represents a nitrogen atom (N) or $CR^5$; $A^6$ represents a nitrogen atom (N) or $CR^6$; $A^7$ represents a nitrogen atom (N) or $CR^7$; $A^8$ represents a nitrogen atom (N) or $CR^8$; $A^9$ represents a nitrogen atom (N) or $CR^9$; and $A^{10}$ represents a nitrogen atom (N) or $CR^{10}$; provided that no more than three of $A^1$, $A^2$, $A^3$, $A^4$, and $A^5$ can be nitrogen atoms, and no more than three of $A^6$, $A^7$, $A^8$, $A^9$, and $A^{10}$ can be nitrogen atoms. Since the A groups are independently selected, the composition can be symmetric or asymmetric. In the case of an asymmetric system, for example, one of the aromatic rings may possess only ring carbon atoms while the other aromatic ring may possess one, two, or three ring nitrogen atoms, or alternatively, for example, one of the aromatic rings may possess a single ring nitrogen atom while the other aromatic ring may possess two or three ring nitrogen atoms. $R^1$, $R^2$, $R^3$, $R^4$, $R^5$, $R^6$, $R^7$, $R^8$, $R^9$, and $R^{10}$ (hereinafter, the "R groups") are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO₂(OR'), —SO₂NR'₂, —P(O)(OR')₂, —P(O)R'(OR'), —P(O)R'₂, —NO₂, —CN, —OCN, —SCN, —NCO, —NCS, —NR'—NR'R', —N₃, —N=C=N—R', —SO₂Cl, —C(O)Cl, and an epoxide group, optionally wherein halo, —OR', —(OCH₂CH₂)ₓ—R', —(OCH₂CH₂)ᵧ—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO₂R', —SO₂(OR'), —SO₂NR'₂, —P(O)(OR')₂, —P(O)R'(OR'), —P(O)R'₂, —NO₂, —CN, —OCN, —SCN, —NCO, —NCS, —NR'—NR'R', —N₃, —N=C=N—R', —SO₂Cl, —C(O)Cl, and the epoxide group are each independently linked to the carbon atom to which it is attached by a —(CH₂)ₙ— linker where n is 1, 2, or 3; or one or two pairs of directly adjacent R¹, R², R³, R⁴, R⁵, R⁶, R⁷, R⁸, R⁹, and R¹⁰ groups are interconnected to form a five- to six-membered substituted or unsubstituted carbocyclic or nitrogen-containing ring; where R' is independently at each occurrence H, C₁-C₆ alkyl, C₃-C₆ cycloalkyl, C₂-C₆ alkenyl, C₅-C₆ cycloalkenyl, C₂-C₆ alkynyl, C₅-C₆ aryl, poly(ethylene glycol), heterocyclyl, or heteroaryl, or wherein two R' groups attached to the same atom are interconnected to form a three- to six-membered ring. The heteroatom-containing functional groups (i.e., "functional groups") may function, for example, to modulate the hydrophilicity or hydrophobicity, serve as a reactive functional group (e.g., to bind to a cell targeting agent), or participate in complexing with the radionuclide. Some examples of functional groups include alkylnyl, halogen atoms (e.g., F, Cl, Br, or I), —OR', —(OCH₂CH₂)ₓ—R' (where x is 1, 2, 3, 4, 5, 6, 7, 8, 9, or 10), —(OCH₂CH₂)ᵧ—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'C(O)NR', —NR'C(S)NR', —S(O)R', —SO₂R', —SO₂(OR'), —SO₂NR'₂, —P(O)(OR')₂, —P(O)R'(OR'), —P(O)R'₂, —NO₂, —CN, —C(O)R', —C(S)R', —OCN, —SCN, —NCO, —NCS, —NR'—NR'R', —N₃, —N=C=N—R', —SO₂Cl, —C(O)Cl, and an epoxide group, or a subset thereof. In any embodiment herein, any one or more of the above functional groups may be excluded or required to be present.

The groups L¹ and L² in Formula (I) are linkers independently selected from —(CH₂)ₚ—, where p is a value of 1, 2, or 3. The subscripts r and s in Formula (I) are independently 0 or 1. When r is 0 or when s is 0, then L¹ or L², respectively, is not present, which results in a direct bond between the respective aromatic ring and the macrocycle.

In any embodiment herein, it may be at least one of R¹, R², R³, R⁴, R⁵, R⁶, R⁷, R⁸, R⁹, and R¹⁰ is a functional group selected from halogen atoms; —OR'; —(OCH₂CH₂)ₓ—R' (where x is 1, 2, 3, 4, 5, 6, 7, 8, 9, or 10); —(OCH₂CH₂)ᵧ—OR' (where y is 1, 2, 3, 4, 5, 6, 7, 8, 9, or 10), —SR'; —OC(O)R'; —C(O)OR'; —C(S)OR'; —C(O)NR'R'; —C(S)NR'R'; —NR'C(O)R'; —NR'C(S)R'; —NR'R'; —NR'C(O)NR'; —NR'C(S)NR'; —S(O)R'; —SO₂R'; —SO₂(OR'); —SO₂NR'₂; —P(O)(OR')₂; —P(O)R'(OR'); —P(O)R'₂; —NO₂; and CN, or a subset thereof (herein referred to as a "first set of functional groups"). In any embodiment herein, it may be at least one of R¹, R², R³, R⁴, R⁵, R⁶, R⁷, R⁸, R⁹, and R¹⁰ is a functional group selected from —C(O)R'; —C(S)R'; —OCN; —SCN; —NCO; —NCS; —NR'—NR'R'; —N₃; —N=C=N—R'; —SO₂Cl; —C(O)Cl; and epoxide groups, or a subset thereof (herein referred to as a "second set of functional groups"). In any embodiment herein, it may be at least one of R¹, R², R³, R⁴, and R⁵ and/or at least one of R⁶, R⁷, R⁸, R⁹, and R¹⁰ is selected from the first set of functional groups. In any embodiment herein, it may be at least one of R¹, R², R³, R⁴, and R⁵ and/or at least one of R⁶, R⁷, R⁸, R⁹, and R¹⁰ is selected from the second set of functional groups. In any embodiment herein, it may be at least one of R¹, R², R³, R⁴, and R⁵ and/or at least one of R⁶, R⁷, R⁸, R⁹, and R¹⁰ is selected from the first set of functional groups, and at least one of R¹, R², R³, R⁴, and R⁵ and/or at least one of R⁶, R⁷, R⁸, R⁹, and R¹⁰ is selected from the second set of functional groups.

It may be that A¹, A², A³, A⁴, and A⁵ are not nitrogen atoms, and/or A⁶, A⁷, A⁸, A⁹, and A¹⁰ are not nitrogen atoms. For example, A¹, A², A³, A⁴, A⁵, A⁶, A⁷, A⁸, A⁹, and A¹⁰ may all not be nitrogen, where the composition is of Formula I-a

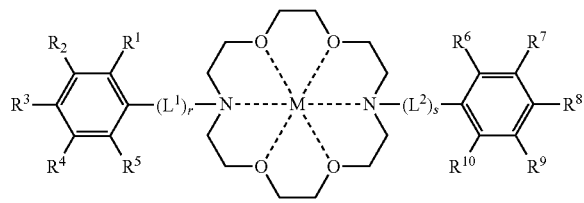

(I-a)

or a pharmaceutically acceptable salt thereof.

In any embodiment herein, it may be at least one of A¹, A², A³, A⁴, A⁵, A⁶, A⁷, A⁸, A⁹, and A¹⁰ is a nitrogen atom. In any embodiment herein, it may be at least one of A¹, A², A³, A⁴, and A⁵ is a nitrogen atom and at least one of A⁶, A⁷, A⁸, A⁹, and A¹⁰ is a nitrogen atom. For example, it may be A¹ or A⁵ and/or A⁶ or A¹⁰ is a nitrogen atom. The following sub-generic structures are exemplary of sub-classes of compositions having a single nitrogen atom in each aromatic ring:

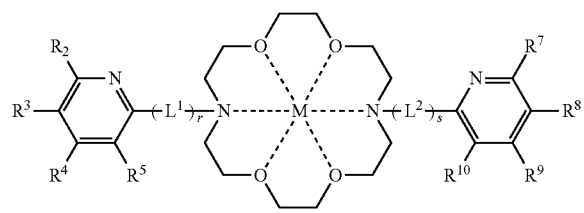

(I-b)

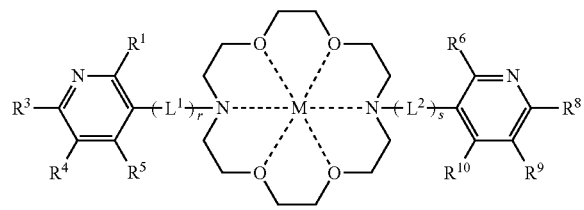

(I-c)

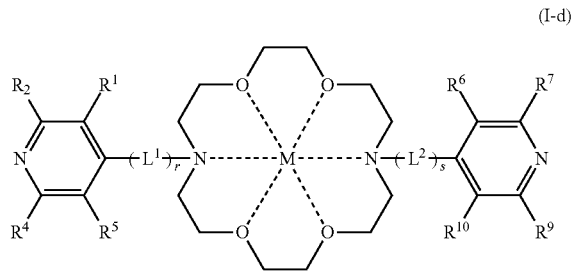

(I-d)

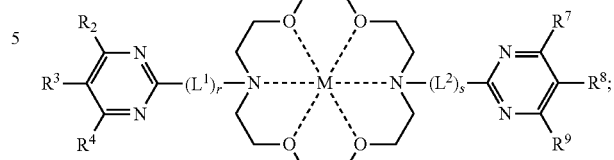

(I-e)

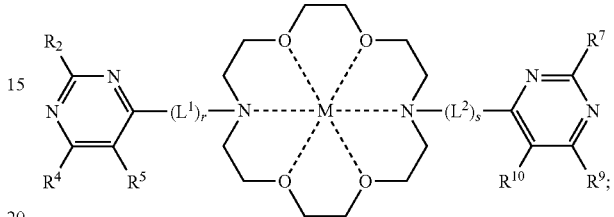

(I-f)

or a pharmaceutically acceptable salt thereof.

In any embodiment herein, it may be any of the above structures takes at least one of the shown R groups as a functional group, or specifically from the first or second set of functional groups, herein also referred to as "first set functional groups" and "second set functional groups," respectively. For example, in Formula (I-b), it may be at least one of $R^2$, $R^3$, $R^4$, $R^5$, $R^7$, $R^8$, $R^9$, and $R^{10}$ is not H. In any embodiment herein, it may be any of the above structures takes at least one of the shown R groups as a first set functional group and at least one of the shown R groups as a second set functional group. For example, in Formula (I-b), it may be at least one of $R^2$, $R^3$, $R^4$, $R^5$, $R^7$, $R^8$, $R^9$, and $R^{10}$ is a first set functional group and at least one of $R^2$, $R^3$, $R^4$, $R^5$, $R^7$, $R^8$, $R^9$, and $R^{10}$ is a second set functional group. In any embodiment herein, it may be at least one of the R groups on one of the aromatic rings and/or at least one of the R groups on the other aromatic ring is a first set functional group. For example, in Formula (I-b), at least one of $R^2$, $R^3$, $R^4$, and $R^5$ and/or at least one of $R^7$, $R^8$, $R^9$, and $R^{10}$ may be a first set functional group. In any embodiment herein, it may be at least one of the R groups on one of the aromatic rings and/or at least one of the R groups on the other aromatic ring is a second set functional group. For example, in Formula (I-b), at least one of $R^2$, $R^3$, $R^4$, and $R^5$ and/or at least one of $R^7$, $R^8$, $R^9$, and $R^{10}$ may be a second set functional group. In any embodiment herein, it may be at least one of the R groups on one of the aromatic rings and/or at least one of the R groups on the other aromatic ring is a first set functional group, and at least one of the R groups on one of the aromatic rings and/or at least one of the R groups on the other aromatic ring is a second set functional group. For example, in Formula (I-b), at least one of $R^2$, $R^3$, $R^4$, and $R^5$ and/or at least one of $R^7$, $R^8$, $R^9$, and $R^{10}$ may be a first set functional group, and at least one of $R^2$, $R^3$, $R^4$, and $R^5$ and/or at least one of $R^7$, $R^8$, $R^9$, and $R^{10}$ may be a second set functional group.

In any embodiment herein, it may be that at least two of $A^1$, $A^2$, $A^3$, $A^4$, $A^5$, $A^6$, $A^7$, $A^8$, $A^9$, and $A^{10}$ are nitrogen atoms. In any embodiment herein, it may be that at least two of $A^1$, $A^2$, $A^3$, $A^4$, and $A^5$ are nitrogen atoms and/or at least two of $A^6$, $A^7$, $A^8$, $A^9$, and $A^{10}$ are nitrogen atoms. In any embodiment herein, it may be that two of $A^1$, $A^2$, $A^3$, $A^4$, and $A^5$ are nitrogen atoms and two of $A^6$, $A^7$, $A^8$, $A^9$, and $A^{10}$ are nitrogen atoms. The following sub-generic structures are exemplary of sub-classes of compositions having two nitrogen atoms in each aromatic ring:

or a pharmaceutically acceptable salt thereof.

In any embodiment herein of Formulas (I-e) and (I-f), it may be at least one of $R^2$, $R^3$, $R^4$, $R^5$, $R^7$, $R^8$, $R^9$, and $R^{10}$ can be a first set functional group or a second set functional group. In any embodiment herein, it may be any of the above structures takes at least one of the shown R groups as a first set functional group and at least one of the shown R groups as a second set functional group. For example, in Formula (I-e), at least one of $R^2$, $R^3$, $R^4$, $R^7$, $R^8$, and $R^9$ may be a first set functional group and at least one of $R^2$, $R^3$, $R^4$, $R^7$, $R^8$, and $R^9$ may be a second set functional group. In any embodiment herein, it may be at least one of the R groups on one of the aromatic rings and/or at least one of the R groups on the other aromatic ring is a first set functional group. For example, in Formula (I-e), at least one of $R^2$, $R^3$, and $R^4$ and/or at least one of $R^7$, $R^8$, and $R^9$ may be a first set functional group. In any embodiment herein, it may be at least one of the R groups on one of the aromatic rings and/or at least one of the R groups on the other aromatic ring is a second set functional group. For example, in Formula (I-e), at least one of $R^2$, $R^3$, and $R^4$ and/or at least one of $R^7$, $R^8$, and $R^9$ may be a second set functional group. In any embodiment herein, it may be at least one of the R groups on one of the aromatic rings and/or at least one of the R groups on the other aromatic ring is a first set functional group, and at least one of the R groups on one of the aromatic rings and/or at least one of the R groups on the other aromatic ring is a second set functional group. For example, in Formula (I-e), at least one of $R^2$, $R^3$, and $R^4$ and/or at least one of $R^7$, $R^8$, and $R^9$ may be a first set functional group, and at least one of $R^2$, $R^3$, and $R^4$ and/or at least one of $R^7$, $R^8$, and $R^9$ may be a second set functional group. An analogous set of examples can be provided for Formula (I-f) by replacing instances of "$R^2$, $R^3$, and $R^4$" with "$R^2$, $R^4$, and $R^5$" and replacing instances of "$R^7$, $R^8$, and $R^9$" with "$R^7$, $R^9$, and $R^{10}$".

In any embodiment herein, it may be at least three of $A^1$, $A^2$, $A^3$, $A^4$, $A^5$, $A^6$, $A^7$, $A^8$, $A^9$, and $A^{10}$ in Formula (I) are nitrogen atoms. For example, at least three of $A^1$, $A^2$, $A^3$, $A^4$, and $A^5$ are nitrogen atoms and/or at least three of $A^6$, $A^7$, $A^8$, $A^9$, and $A^{10}$ may be nitrogen atoms. The following sub-generic structure is exemplary of a sub-class of compositions having three nitrogen atoms in each aromatic ring:

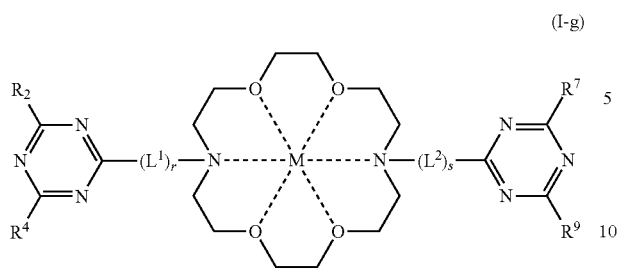

(I-g)

or a pharmaceutically acceptable salt thereof.

In any embodiment herein of Formula (I-g), at least one of $R^2$, $R^4$, $R^7$, and $R^9$ may be a first set functional group or a second set functional group. In any embodiment herein of Formula (I-g), it may be at least one of $R^2$, $R^4$, $R^7$, and $R^9$ can be a first set functional group and at least one $R^2$, $R^4$, $R^7$, and $R^9$ can be a second set functional group. In any embodiment herein of Formula (I-g), it may be at least one of $R^2$ and $R^4$ and/or at least one of $R^7$ and $R^9$ is a first set functional group. In any embodiment herein of Formula (I-g), it may be at least one of $R^2$ and $R^4$ and/or at least one of $R^7$ and $R^9$ is a second set functional group. In any embodiment herein of Formula (I-g), it may be at least one of $R^2$ and $R^4$ and/or at least one of $R^7$ and $R^9$ is a first set functional group, and at least one of $R^2$ and $R^4$ and/or at least one of $R^7$ and $R^9$ is a second set functional group.

In any embodiment herein, it may be that at least one of the A groups in at least one of the aromatic rings in Formula (I) is a carbon atom having a first set functional group appended thereto as an R group. In any embodiment herein, it may be that at least one of the A groups in each of the aromatic rings is a carbon atom having a first set functional group appended thereto as an R group. For example, in Formula (I), (I-a), or (I-b), $A^2$ and/or $A^7$ (or equivalently, $A^4$ and/or $A^9$) may carbon atoms having a first set functional group appended thereto. As another example, in the case where $A^1$ and/or $A^6$ (or equivalently, $A^5$ and/or $A^{10}$) are carbon atoms, the carbon atoms may have a first set functional group appended thereto. The following sub-generic structures are exemplary of some of the above-described compositions:

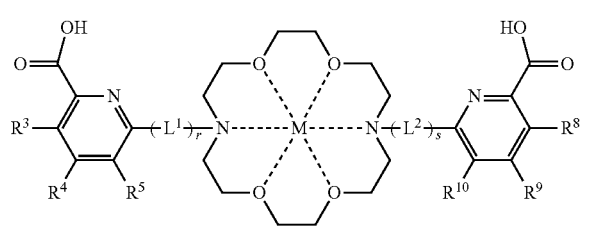

(I-h)

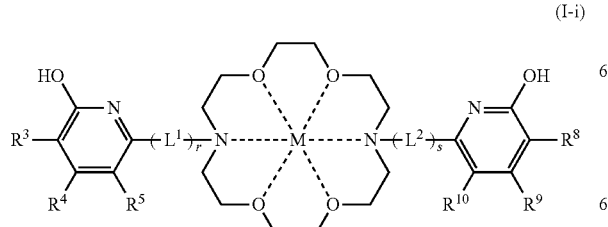

(I-i)

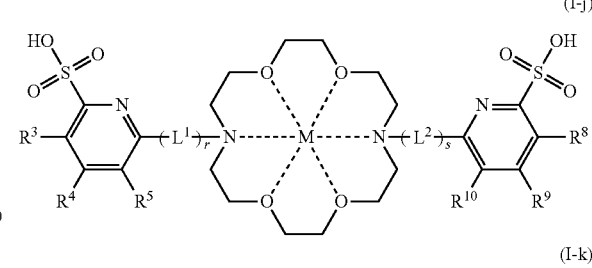

(I-j)

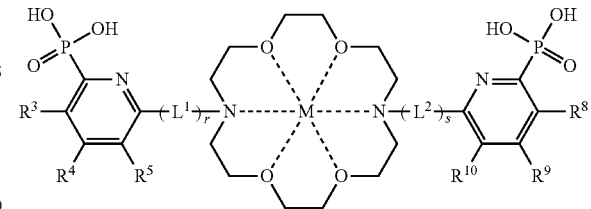

(I-k)

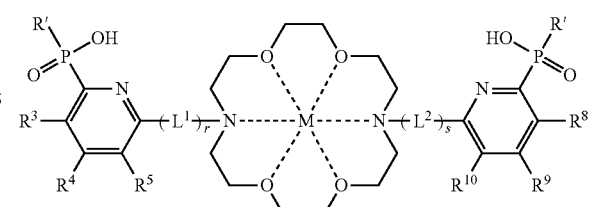

(I-m)

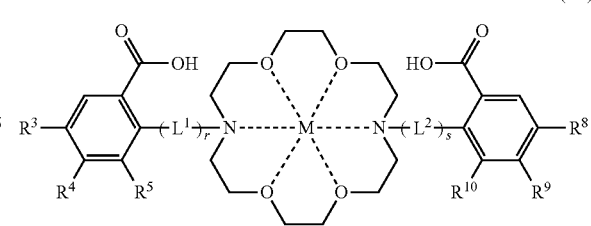

(I-n)

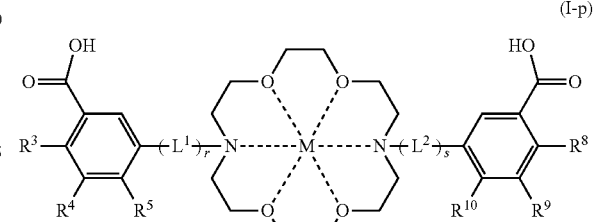

(I-p)

or a pharmaceutically acceptable salt thereof.

The structure may also be asymmetric in the choice of functional group, such as provided in the following exemplary structure:

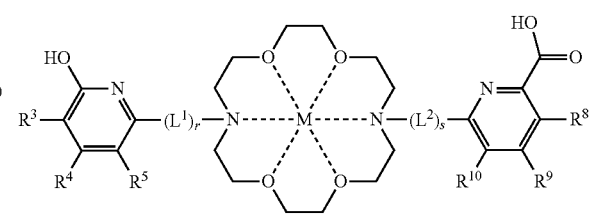

(I-q)

or a pharmaceutically acceptable salt thereof.

In any embodiment herein, it may be that at least one of the A groups in at least one of the aromatic rings in Formula (I) is a carbon atom having a second set functional group appended thereto as an R group. In any embodiment herein, it may be that at least one of the A groups in each of the aromatic rings is a carbon atom having a second set functional group appended thereto as an R group, or only one of the aromatic rings contains at least one second set functional group. In any embodiment herein, it may be that the second set functional group is specifically located at $A^2$, $A^3$, or $A^4$, or at $A^7$, $A^8$ or $A^9$, or more specifically, at $A^3$ or $A^8$. The following sub-generic structures are exemplary of some of the above-described compositions containing at least one second set functional group:

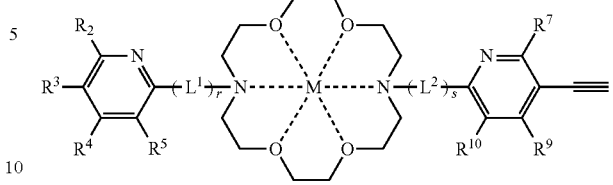

(I-r)

(I-s)

(I-s')

(I-t)

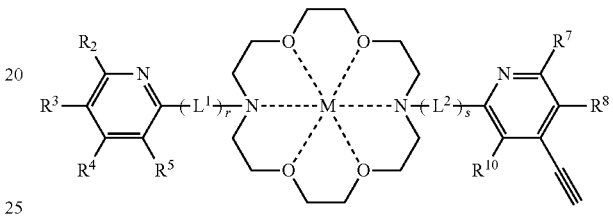

(I-u)

(I-u')

or a pharmaceutically acceptable salt thereof.

In any embodiment herein, it may be that at least one of the R groups in any of the above structures on the aromatic rings is a first set functional group. In any embodiment herein, it may be that the first set functional group is in the same ring containing the second set functional group.

In any embodiment herein, it may be that one or two pairs of directly adjacent groups among $R^1$, $R^2$, $R^3$, $R^4$, $R^5$, $R^6$, $R^7$, $R^8$, $R^9$, and $R^{10}$ groups are interconnected to form a four- to six-membered carbocyclic or nitrogen-containing ring optionally substituted with one or more groups provided above for $R^1$, $R^2$, $R^3$, $R^4$, $R^5$, $R^6$, $R^7$, $R^8$, $R^9$, and $R^{10}$, wherein the interconnection of $R^1$, $R^2$, $R^3$, $R^4$, $R^5$, $R^6$, $R^7$, $R^8$, $R^9$, and $R^{10}$ groups results in a fused ring system that includes the ring shown in Formula (I) containing $A^1$, $A^2$, $A^3$, $A^4$, and $A^5$, and/or results in a fused ring system that includes the ring shown in Formula (I) containing $A^6$, $A^7$, $A^8$, $A^9$, and $A^{10}$.

In any embodiment herein, it may be that the structures include at least one fused ring system that contains at least one of the shown aromatic rings containing the A groups. A sub-generic structure exemplary of such structures is provided as follows:

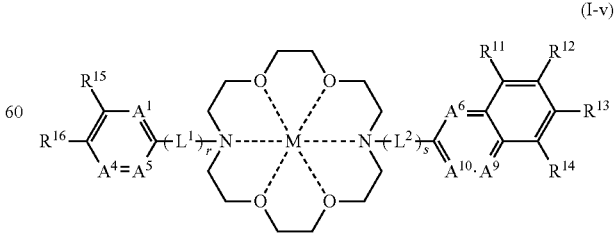

(I-v)

or a pharmaceutically acceptable salt thereof.

In Formula (I-v), $A^1$, $A^4$, $A^5$, $A^6$, $A^9$, $A^{10}$, $L^1$, $L^2$, r, s, and M are as provided in any embodiment herein, and $R^{11}$, $R^{12}$, $R^{13}$, $R^{14}$, $R^{15}$, and $R^{16}$ are independently selected from the group consisting of H, alkyl, cycloalkyl, alkenyl, cycloalkenyl, alkynyl, aryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3; and wherein R' is independently at each occurrence H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl. In any embodiment herein, the groups $R^{15}$ and $R^{16}$ may optionally interconnect to form a second fused ring, which may be the same or different from the first fused ring. In any embodiment herein, it may be that $R^{11}$, $R^{12}$, $R^{13}$, and $R^{14}$ do not further interconnect, which leaves the fused ring as a bicyclic fused ring system; however, in any embodiment herein, it may be that two adjacent groups from among $R^{11}$, $R^{12}$, $R^{13}$, and $R^{14}$ can interconnect, thereby forming a tricyclic fused ring system.

In any embodiment herein of Formula (I-v), it may be that at least one of $R^{11}$, $R^{12}$, $R^{13}$, $R^{14}$, $R^{15}$, and $R^{16}$ is a group selected from —C(O)R'; —C(S)R'; —OCN; —SCN; —NCO; —NCS; —NR'—NR'R'; —N$_3$; —N=C=N—R'; —SO$_2$Cl; —C(O)Cl; and an epoxide group. In any embodiment herein of Formula (I-v), it may be that at least one of $R^{11}$, $R^{12}$, $R^{13}$, $R^{14}$, $R^{15}$, and $R^{16}$ is a group selected from halogen atoms; —OR'; —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR'; —OC(O)R'; —C(O)OR'; —C(S)OR'; —C(O)NR'R'; —C(S)NR'R'; —NR'C(O)R'; —NR'C(S)R'; —NR'R'; —NR'C(O)NR'; —NR'C(S)NR'; —S(O)R'; —SO$_2$R'; —SO$_2$(OR'); —SO$_2$NR'$_2$, —P(O)(OR')$_2$; —P(O)R'(OR'); —P(O)R'$_2$, —NO$_2$; and —CN.

In any embodiment herein, it may be that the structures include two fused ring systems that contain each of the shown aromatic rings containing the A groups. A sub-generic structure exemplary of such structures is provided as follows:

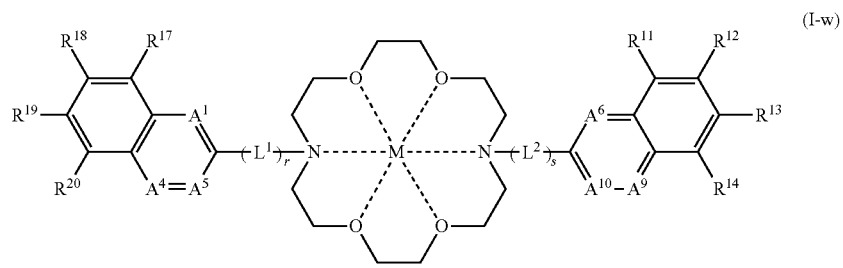

(I-w)

or a pharmaceutically acceptable salt thereof.

In Formula (I-w), $A^1$, $A^4$, $A^5$, $A^6$, $A^9$, $A^{10}$, $L^1$, $L^2$, r, s, and M are as defined above, and $R^{11}$, $R^{12}$, $R^{13}$, $R^{14}$, $R^{17}$, $R^{18}$, $R^{19}$, and $R^{20}$ are independently selected from the group consisting of H, alkyl, cycloalkyl, alkenyl, cycloalkenyl, alkynyl, aryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_x$-linker where n is 1, 2, or 3; and wherein R' is independently at each occurrence H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl.

In any embodiment herein of Formula (I-w), it may be at least one of $A^1$, $A^4$, $A^5$, $A^6$, $A^9$, and $A^{10}$ is a nitrogen atom. In any embodiment herein of Formula (I-w), it may be at least one (i.e., one, two, or all) of $A^1$, $A^4$, and $A^5$ is a nitrogen atom and at least one (i.e., one, two, or all) of $A^6$, $A^9$, and $A^{10}$ is a nitrogen atom. A sub-generic structure exemplary of such structures is provided as follows:

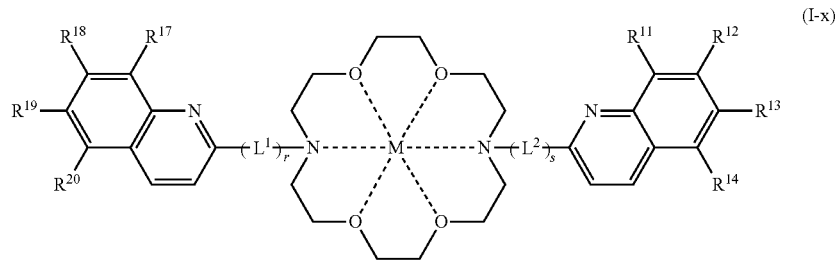

(I-x)

or a pharmaceutically acceptable salt thereof.

In another aspect, the present technology provides a composition useful in the targeted radiotherapy of cancer. The composition targets (i.e., selectively binds to) cancer cells by including in its structure a selective cancer cell targeting group which selectively directs the composition to cancer cells. The composition can be conveniently expressed by Formula (I) except that at least one of the R groups includes a selective cancer cell targeting group. The selective cancer cell targeting group can be any group known in the art capable of selectively targeting cancer cells. By way of example, the selective cancer cell targeting group may target receptor sites specific to cancer cells. The cancer cell targeting group may be composed of amino acids linked by peptide bonds. The selective cancer cell targeting group of any embodiment herein may include a cancer-targeting antibody, antibody fragment, a selective targeting oligopeptide containing up to 50 amino acids, an enzyme, a nucleobase-containing moiety (such as an oligonucleotide, DNA or RNA vector, or aptamer), or a lectin. In any embodiment herein, any of the foregoing cancer cell targeting agents may be bound or adsorbed onto a particle (e.g., a nanoparticle or microparticle), with the particle bound to one of the aromatic rings of the macrocyclic composition via a reactive functional group.

The targeting composition is represented by Formula (II)

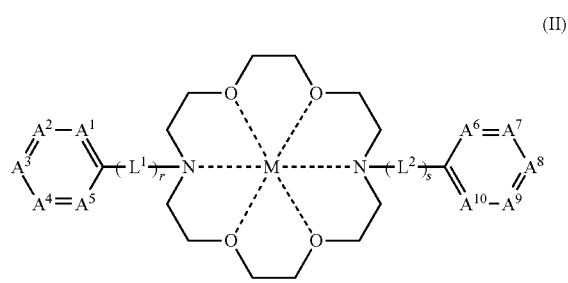

(II)

In Formula (II), $A^1$-$A^{10}$, M, $L^1$, $L^2$, r, and s have the same meanings provided for any embodiment herein with the exception that at least one of the R groups ($R^1$-$R^{10}$ is or includes a selective cancer cell targeting group, which may be any one or more of the selective cancer cell targeting groups provided above including a particle containing such groups. In particular, at least one of $R^1$, $R^2$, $R^3$, $R^4$, $R^5$, $R^6$, $R^7$, $R^8$, $R^9$, and $R^{10}$ is a selective cancer cell targeting group or a selective cancer cell targeting group linked to the carbon atom to which it is attached by a alkylene, —O—, —S—, —(OCH$_2$CH$_2$)$_z$— (where z is 1, 2, 3, 4, 5, 6, 7, 8, 9, or 10), —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')—, optionally wherein —O—, —S—, —(OCH$_2$CH$_2$)$_z$—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')— are each independently linked to the carbon atom to which it is attached by a $C_1$-$C_3$ alkylene. Thus, Formula (II) includes the same number of sub-generic structures under Formula (I), except that at least one of the R groups ($R^1$-$R^{10}$) is or includes a selective cancer cell targeting group. An analogous series of sub-generic structures under Formula (II) are derived from Formulas (I-a) to (I-x) by requiring at least one of the R groups ($R^1$-$R^{10}$) in each of these sub-generic formulas to include a selective cancer cell targeting group. The sub-generic structures under Formula (II) can thus be identified as Formulas (II-a) to (II-x), in analogy to Formulas (II-a) to (II-x).

In another aspect, methods of producing the composition according to Formula (I) and Formula (II) are provided. In such methods, aromatic rings can be attached to the macrocyclic portion by methods well known in the art to produce a ligand moiety, which corresponds to the structure shown in Formula (I) or Formula (II), except without the alpha-emitting radionuclide M. The ligand is then complexed with the radionuclide by methods well known in the art. Functional groups, such as any of those provided for $R^1$-$R^{10}$, are typically present on the aromatic rings, often in protected form, when the aromatic rings are being attached to the macrocyclic portion; however, in some cases, the aromatic rings may be attached to the macrocyclic portion before being functionalized with any of the functional groups provided for $R^1$-$R^{10}$. To produce the composition under Formula (II), a composition under Formula (I) containing at least one reactive functional group is reacted with a selective cancer cell targeting group to bind the selective cancer cell targeting group, via the reactive functional group, to the aromatic ring attached to the macrocyclic portion. For example, an isocyanate or isothiocyanate reactive functional group can be included on at least one aromatic ring of the composition in Formula (I), and the resulting functionalized composition appended to an amino acid-containing targeting agent by reaction of the isocyanate or isothiocyanate group with amino groups in the amino acid-containing targeting agent to produce a targeting composition of Formula (II). In this way, the amino-containing targeting agent becomes bound to the macrocyclic complex by a urea or thiourea linkage. Numerous other modes of attachment, with different linkages, are possible depending on the reactive functional group used. The attachment of the selective cancer cell targeting group may be performed on the uncomplexed or complexed form of Formula (I). Significantly, the uncomplexed form of Formula (I) can be complexed with a radionuclide at room temperature (generally 18-30° C., or about or no more than 20° C., 25° C., or 30° C.) at high radiochemical yields, e.g., at least or greater than 90%, 95%, 97%, or 98%.

Since the targeting composition according to Formula (II) contains a targeting agent, as attached by reaction of the reactive functional group with the targeting agent, the target composition according to Formula (II) generally does not include substantially reactive functional groups, such as those used for attaching the targeting agent in the first place. Thus, in any embodiment herein, the targeting composition according to Formula (II) may include any of the groups listed for $R^1$-$R^{10}$ under Formula (I), except the reactive functional groups found in the second set functional groups.

The present technology also provides compositions (e.g., pharmaceutical compositions) and medicaments comprising any of one of the embodiments of the compounds of Formula II (or a pharmaceutically acceptable salt thereof) disclosed herein and a pharmaceutically acceptable carrier or one or more excipients or fillers (collectively referred to as "pharmaceutically acceptable carrier" unless otherwise specified). The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of e.g., prostate cancer, breast cancer, or bladder cancer. Another example of an effective amount includes amounts or dosages that are capable of reducing symptoms associated with e.g., prostate cancer, breast cancer, or bladder cancer, such as, for example, reduction in proliferation and/or metastasis of prostate cancer, breast cancer, or bladder cancer. The effective amount may be from about 0.01 µg to about 1 mg of the compound per gram of the composition, and preferably from about 0.1 µg to about 500 µg of the compound per gram of the composition. As used herein, a "subject" or "patient" is a mammal, such as a cat, dog, rodent or primate. Typically the subject is a human, and, preferably, a human suffering from or suspected of suffering from non-small cell lung cancer, bladder cancer, or colon cancer (such as colon adenocarcinoma). The term "subject" and "patient" can be used interchangeably.

In any of the embodiments of the present technology described herein, the pharmaceutical composition may be packaged in unit dosage form. The unit dosage form is effective in treating non-small cell lung cancer, bladder cancer, or colon cancer (such as colon adenocarcinoma). Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

The pharmaceutical compositions may be prepared by mixing one or more compounds of Formulas II, pharmaceutically acceptable salts thereof, stereoisomers thereof, tautomers thereof, or solvates thereof, with pharmaceutically acceptable carriers, excipients, binders, diluents or the like to prevent and treat disorders associated with cancer (e.g., prostate cancer, breast cancer, or bladder cancer). The compounds and compositions described herein may be used to prepare formulations and medicaments that treat e.g., prostate cancer, breast cancer, or bladder cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. The instant compositions may also include, for example, micelles or liposomes, or some other encapsulated form.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For the indicated condition, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In another aspect, the present technology provides a method of treating cancer by administering an effective amount of the targeting composition according to Formula (II) to a subject having cancer. Since a cancer cell targeting agent can be selected to target a wide variety of cancers, the cancer considered herein for treatment is not limited. The cancer can be essentially any type of cancer. For example, antibodies or peptide vectors can be produced to target any of a wide variety of cancers. The targeting compositions described herein are typically administered by injection into the bloodstream, but other modes of administration, such as oral or topical administration, are also considered. In some embodiments, the targeting composition may be administered locally, at the site where the target cells are present, i.e., in a specific tissue, organ, or fluid (e.g., blood, cerebrospinal fluid, etc.). Any cancer that can be targeted through the bloodstream is of particular consideration herein. Some examples of applicable body parts containing cancer cells include the breasts, lungs, stomach, intestines, prostate, ovaries, cervix, pancreas, kidney, liver, skin, lymphs, bones, bladder, uterus, colon, rectum, and brain. The cancer can also include the presence of one or more carcinomas, sarcomas, lymphomas, blastomas, or teratomas (germ cell tumors). The cancer may also be a form of leukemia. In some embodiments, the cancer is a triple negative breast cancer.

As is well known in the art, the dosage of the active ingredient(s) generally depends on the disorder or condition being treated, the extent of the disorder or condition, the method of administration, size of the patient, and potential side effects. In different embodiments, depending on these and other factors, a suitable dosage of the targeting composition may be precisely, at least, above, up to, or less than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

The examples herein are provided to illustrate advantages of the present technology and to further assist a person of ordinary skill in the art with preparing or using the compounds of the present technology or salts, pharmaceutical compositions, derivatives, prodrugs, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Examples

Exemplary Synthetic Procedures and Characterization

Materials and Instrumentation. All solvents and reagents, unless otherwise noted, were purchased from commercial sources and used as received without further purification. Solvents noted as "dry" were obtained following storage over 3 Å molecular sieves. Metal salts were purchased from Strem Chemicals (Newburyport, Mass.) and were of the highest purity available; $Lu(ClO_4)_3$ was provided as an aqueous solution containing 15.1 wt % Lu. The bifunctional ligand p-SCN-Bn-DOTA was purchased from Macrocyclics (Plano, Tex.). NMe$_4$OH was purchased as a 25 wt % solution in H$_2$O (trace metals basis, Beantown Chemical, Hudson, N.H.). Hydrochloric acid (BDH Aristar Plus, VWR, Radnor, Pa.) and nitric acid (Optima, ThermoFisher Scientific, Waltham, Mass.) were of trace metals grade. Both Chelex 100 (sodium form, 50-100 mesh) and human serum used for $^{225}$Ac-complex challenge assays were purchased from Sigma Aldrich (St. Louis, Mo.). Deionized water (≥18 MΩ cm) was prepared on site using either Millipore Direct-Q® 3UV or Elga Purelab Flex 2 water purification systems.

Reactions were monitored by thin-layer chromatography (TLC, Whatman UV254 aluminum-backed silica gel). The HPLC system used for analysis and purification of compounds consisted of a CBM-20A communications bus module, an LC-20AP (preparative) or LC-20AT (analytical) pump, and an SPD-20AV UV/Vis detector monitoring at 270 nm (Shimadzu, Japan). Analytical chromatography was carried out using an Ultra Aqueous C18 column, 100 Å, 5 μm, 250 mm×4.6 mm (Restek, Bellefonte, Pa.) at a flow rate of 1.0 mL/min, unless otherwise noted. Purification was performed with an Epic Polar preparative column, 120 Å, 10 μm, 25 cm×20 mm (ES Industries, West Berlin, N.J.) at a flow rate of 14 mL/min, unless otherwise noted. Gradient HPLC methods were employed using a binary mobile phase that contained H$_2$O (A) and either MeOH (B) or ACN (C). HPLC Method A: 10% B (0-5 min), 10-100% B (5-25 min). Method B: 10% C (0-5 min), 10-100% C (5-25 min). Method C: 10% C (0-5 min), 10-100% C (5-40 min). Method D: 10% C (0-5 min), 10-100% C (5-20 min). The solvent systems contained 0.1% trifluoroacetic acid (TFA), except for Method C, in which 0.2% TFA was used. NMR spectra were recorded at ambient temperature on Varian Inova 300 MHz, 400 MHz, 500 MHz or 600 MHz spectrometers, or on a Bruker AV III HD 500 MHz spectrometer equipped with a broadband Prodigy cryoprobe. Chemical shifts are reported in ppm. $^1$H and $^{13}$C NMR spectra were referenced to the TMS internal standard (0 ppm), to the residual solvent peak, or to an acetonitrile internal standard (2.06 ppm in D$_2$O spectra). $^{19}$F NMR spectra were referenced to a monofluorobenzene internal standard (−113.15 ppm). The splitting of proton resonances in the reported $^1$H spectra is defined as: s=singlet, d=doublet, t=triplet, q=quartet, m=multiplet, dt=doublet of triplets, td=triplet of doublets, and br=broad. IR spectroscopy was performed on a KBr pellet of sample using a Nicolet Avatar 370 DTGS (ThermoFisher Scientific, Waltham, Mass.). High-resolution mass spectra (HRMS) were recorded on an Exactive Orbitrap mass spectrometer in positive ESI mode (ThermoFisher Scientific, Waltham, Mass.). UV/visible spectra were recorded on a Cary 8454 UV-Vis (Agilent Technologies, Santa Clara, Calif.) using 1-cm quartz cuvettes, unless otherwise noted. Elemental analysis (EA) was performed by Atlantic Microlab, Inc. (Norcross, Ga.).

Synthesis and Characterization of Macropa Complexes, Macropa-NCS, and Macropa-NHC(S)NHCH$_3$. N,N'-bis[(6-carboxy-2-pyridil)methyl]-4,13-diaza-18-crown-6 (H$_2$macropa.2HCl.4H$_2$O)[102,103] was prepared using 1,7,10,16-tetraoxa-4,13-diazacyclooctadecane (7) that was either purchased from EMD Millipore (Darmstadt, Germany) or synthesized via literature protocols.[104] Chelidamic acid monohydrate (1) was purchased from TCI America (Portland, Oreg.). Dimethyl 4-chloropyridine-2,6-dicarboxylate (2),[105] dimethyl 4-azidopyridine-2,6-dicarboxylate (3),[106] and 6-chloromethylpyridine-2-carboxylic acid methyl ester (8),[102] were prepared via the indicated literature protocols.

Preparation of [La(macropa)]$^{2+}$

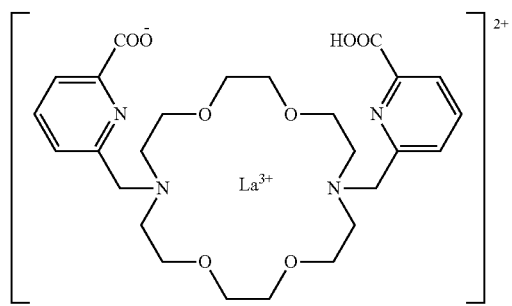

To a suspension of H$_2$macropa.2HCl.4H$_2$O (0.0233 g, 0.034 mmol) in 2-propanol (0.6 mL) was added triethylamine (20 μL, 0.143 mmol). The pale-gold solution was heated at reflux for 25 min before a solution of La(ClO$_4$)$_3$.6H$_2$O (0.0209 g, 0.038 mmol) in 2-propanol (0.5 mL) was added dropwise. A precipitate formed immediately. The cream suspension was stirred at reflux for an additional 1.5 h before it was cooled and centrifuged. The supernatant was removed, and the pellet was washed with 2-propanol (2×1 mL) and then air-dried on filter paper to give the title complex as a pale-tan solid (0.0177 g) containing 0.64 equiv of 2-propanol. $^1$H NMR (500 MHz, D$_2$O, pD≈9) δ=7.87 (t, J=7.8 Hz, 2H), 7.54 (d, J=7.8 Hz, 2H), 7.39 (d, J=7.6 Hz, 2H), 5.21 (d, J=15.7 Hz, 2H), 4.44 (t, J=11.6 Hz, 2H), 4.09 (t, J=11.2 Hz, 4H), 4.01 (t, J=10.4 Hz, 2H), 3.74 (d, J=9.9 Hz, 2H), 3.65-3.60 (m, 4H), 3.58-3.47 (m, 4H), 3.44 (d, J=10.8 Hz, 2H), 2.75 (td, J=13.1, 2.7 Hz, 2H), 2.56 (d, J=13.9 Hz, 2H), 2.38 (d, J=14.0 Hz, 2H). $^{13}$C{$^1$H} APT NMR (126 MHz, D$_2$O, pD≈9) δ=172.62, 158.70, 150.19, 140.94, 126.89, 122.32, 71.88, 70.12, 69.20, 68.05, 60.14, 56.08, 54.01. EA Found: C, 35.16; H, 4.73; N, 5.91. Calc. for C$_{26}$H$_{35}$LaN$_4$O$_8$.2ClO$_4$.2H$_2$O.0.64iPrOH: C, 35.53; H, 4.71; N, 5.94. IR (cm$^{-1}$): 3443, 2913, 1630, 1596, 1461, 1370, 1265, 1083, 948, 839, 770, 678, 617, 513. HPLC t$_R$=18.104 min (Method A). HRMS (m/z): 669.14289, 335.07519; Calc for [C$_{26}$H$_{34}$LaN$_4$O$_8$]$^+$ and [C$_{26}$H$_{35}$LaN$_4$O$_8$]$^{2+}$, respectively: 669.14346, 335.07537.

Preparation of [Lu(macropa)]$^+$

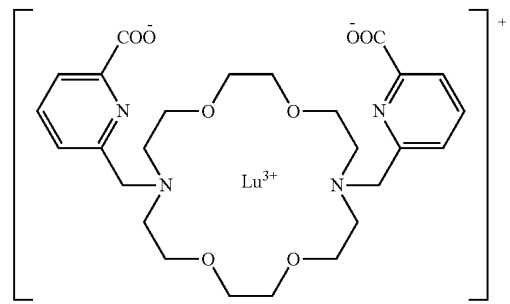

To a suspension H$_2$macropa.2HCl.4H$_2$O (0.0730 g, 0.108 mmol) in 2-propanol (2 mL) was added triethylamine (61.5

μL, 0.441 mmol). The pale-gold solution was heated at reflux for 25 min before a solution of aq. Lu(ClO$_4$)$_3$ (0.1372 g, 0.118 mmol Lu) in 2-propanol (1.8 mL) was added dropwise. A precipitate formed immediately. After stirring at reflux or an additional 1 h, the cream suspension was triturated at RT for 20 h and then centrifuged. The supernatant was removed, and the pellet was washed with 2-propanol (2×2 mL) and then air-dried on filter paper to give the title complex as a pale-tan solid (0.0605 g) containing residual 2-propanol and triethylamine salt. $^1$H NMR (600 MHz, D$_2$O, pD≈7-8) δ=7.85 (t, J=7.7 Hz, 2H), 7.52 (d, J=7.8 Hz, 2H), 7.37 (d, J=7.6 Hz, 2H), 4.68 (d, J=16.3 Hz, 2H), 4.56 (td, J=11.2, 1.7 Hz, 2H), 4.42-4.38 (m, 2H), 4.23-4.19 (m, 6H), 4.07 (d, J=16.3 Hz, 2H), 3.96-3.87 (m, 2H), 3.71-3.63 (m, 4H), 3.38 (td, J=10.0, 4.7 Hz, 2H), 3.00 (m, 2H), 2.93 (d, J=13.1 Hz, 2H), 2.52 (dt, J=14.8, 4.5 Hz, 2H). $^{13}$C{$^1$H} APT NMR (126 MHz, D$_2$O, pD≈7-8) δ=172.13, 158.67, 148.98, 141.81, 127.38, 122.83, 75.33, 73.12, 71.97, 71.70, 64.65, 57.37, 55.08. IR (cm$^{-1}$): 3400, 1639, 1396, 1274, 1091, 913, 770, 678, 622. HPLC t$_R$=not stable (Method A). HRMS (m/z): 705.17772; Calc for [C$_{26}$H$_{34}$LuN$_4$O$_8$]$^+$: 705.17788.

Preparation of dimethyl 4-aminopyridine-2,6-dicarboxylate (4)

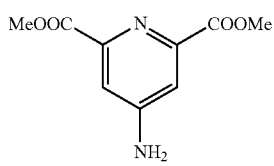

4

Dimethyl 4-azidopyridine-2,6-dicarboxylate (3, 0.9445 g, 4.0 mmol), 10% Pd/C (0.1419 g), and DCM:MeOH (1:1, 18 mL) were combined in a round-bottom flask. After purging the flask with a balloon of H$_2$, the reaction was stirred vigorously at room temperature under an H$_2$ atmosphere for 46 h. The gray mixture was diluted with DMF (450 mL) and filtered through a bed of Celite. Following a subsequent filtration through a 0.22 μm nylon membrane, the filtrate was concentrated at 60° C. under reduced pressure and further dried in vacuo to obtain 4 as a pale-tan solid (0.824 g, 98% yield). $^1$H NMR (500 MHz, DMSO-d$_6$): δ=7.36 (s, 2H), 6.72 (s, 2H), 3.84 (s, 6H). $^{13}$C{$^1$H} APT NMR (126 MHz, DMSO-d6): δ=165.51, 156.24, 148.05, 111.99, 52.29. IR (cm$^{-1}$): 3409, 3339, 3230, 1726, 1639, 1591, 1443, 1265, 996, 939, 787, 630, 543. HPLC t$_R$=9.369 min (Method B). HRMS (m/z): 211.07213 [M+H]$^+$; Calc: 211.07133.

Preparation of Ethyl 4-amino-6-(hydroxymethyl)picolinate (5)

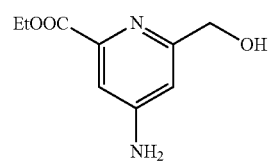

5

To a refluxing suspension of 4 (0.677 g, 3.22 mmol) in absolute EtOH (27 mL) was added NaBH$_4$ (0.1745 g, 4.61 mmol) portionwise over 1 h to give a pale-yellow suspension. The reaction was then quenched with acetone (32 mL) and concentrated at 60° C. under reduced pressure to a tan solid. The crude product was dissolved in H$_2$O (60 mL) and washed with ethyl acetate (4×150 mL). The combined organics were dried over sodium sulfate and concentrated at 40° C. under reduced pressure. Further drying in vacuo yielded 5 as a pale-yellow solid (0.310 g, 49% yield). $^1$H NMR (300 MHz, DMSO-d$_6$): δ=7.07 (d, J=2.1 Hz, 1H), 6.78 (m, 1H), 6.32 (s, 2H), 5.30 (t, J=5.8 Hz, 1H), 4.39 (d, J=5.6 Hz, 2H), 4.26 (q, J=7.1 Hz, 2H), 1.28 (t, J=7.1 Hz, 3H). $^{13}$C APT NMR (126 MHz, DMSO-d$_6$) δ=165.57, 162.38, 155.68, 147.25, 108.50, 107.01, 63.95, 60.61, 14.24. IR (cm$^{-1}$): 3439, 3217, 2974, 2917, 1717, 1643, 1600, 1465, 1396, 1378, 1239, 1135, 1022, 974, 865, 783. HPLC t$_R$=8.461 min (Method B). HRMS (m/z): 197.09288 [M+H]$^+$; Calc: 197.09207.

Preparation of Ethyl 4-amino-6-(chloromethyl)picolinate (6)

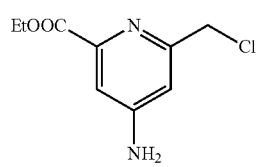

6

A mixture of thionyl chloride (2.5 mL) and 5 (0.301 g, 1.53 mmol) was stirred in an ice bath for 1 h, and then at RT for 30 min. The yellow-orange emulsion was concentrated at 40° C. under reduced pressure to an oily residue. The residue was neutralized with sat. aq. NaHCO$_3$ (12 mL) and then extracted with ethyl acetate (75 mL). The organic extract was washed with H$_2$O (2 mL), dried over sodium sulfate, and concentrated at 40° C. under reduced pressure. Further drying in vacuo gave 6 as an amber wax (0.287 g, 80% yield, corrected for residual ethyl acetate). $^1$H NMR (500 MHz, DMSO-d$_6$) δ=7.18 (d, J=2.1 Hz, 1H), 6.78 (d, J=2.1 Hz, 1H), 6.62 (br s, 2H), 4.62 (s, 2H), 4.29 (q, J=7.1 Hz, 2H), 1.30 (t, J=7.1 Hz, 3H). $^{13}$C{$^1$H} APT NMR (126 MHz, DMSO-d$_6$) δ=164.75, 156.42, 156.19, 147.17, 109.79, 109.50, 60.97, 46.47, 14.15. IR (cm$^{-1}$): 3452, 3322, 3209, 2978, 2922, 1726, 1639, 1604, 1513, 1465, 1378, 1248, 1126, 1026, 983, 861, 783, 752, 700. HPLC t$_R$=12.364 min (Method B). HRMS (m/z): 215.05903 [M+H]$^+$; Calc: 215.05818.

Preparation of Methyl 6-((1,4,10,13-tetraoxa-7,16-diazacyclooctadecan-7-yl)methyl)picolinate (9.2TFA.1H$_2$O)

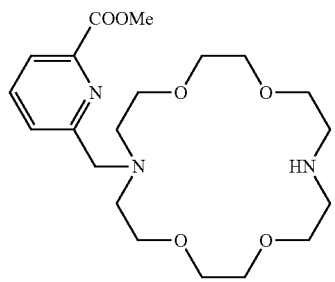

To a clear and colorless solution of 1,7,10,16-tetraoxa-4,13-diazacyclooctadecane (7, 1.9688 g, 7.5 mmol) and diisopropylethylamine (0.8354 g, 6.5 mmol) in dry ACN (1.075 L) at 75° C. was added dropwise a solution of 6 (0.9255 g, 5.0 mmol) in dry ACN (125 mL) over 2 h 40 min. The flask was then equipped with a condenser and drying tube, and the slightly-yellow solution was heated at reflux for 42 h. Subsequently, the dark-gold solution containing fine, white precipitate was concentrated at 60° C. under reduced pressure to an amber oil. To the crude oil was added 10% MeOH/H$_2$O containing 0.1% TFA (10 mL). The slight suspension was filtered, and the filtrate was purified by preparative HPLC (Method A). Pure fractions were combined, concentrated at 60° C. under reduced pressure, and then lyophilized to give 9 (1.6350 g, 50% yield) as a pale-orange solid. $^1$H NMR (500 MHz, DMSO-d$_6$) δ=8.75 (br s, 2H), 8.17-8.06 (m, 2H), 7.83 (dd, J=7.4, 1.5 Hz, 1H), 4.68 (br s, 2H), 3.91 (s, 3H), 3.85 (br t, J=5.1 Hz, 4H), 3.69 (t, J=5.1 Hz, 4H), 3.59 (br s, 8H), 3.50 (br s, 4H), 3.23 (br t, J=5.1 Hz, 4H). $^{13}$C {$^1$H} APT NMR (126 MHz, DMSO-d$_6$) δ 164.68, 158.78-157.98 (q, TFA), 151.44, 147.13, 139.01, 128.63, 124.87, 120.08-113.01 (q, TFA), 69.33, 69.00, 65.31, 64.60, 56.43, 53.29, 52.67, 46.32. $^{19}$F NMR (470 MHz, DMSO-d$_6$) δ=−73.84. EA Found: C, 43.88; H, 5.29; N, 6.28. Calc. for C$_{20}$H$_{33}$N$_3$O$_6$.2CF$_3$COOH.1H$_2$O: C, 43.84; H, 5.67; N, 6.39. HPLC t$_R$=12.372 min (Method B). HRMS (m/z): 412.24568 [M+H]$^+$; Calc: 412.24421.

Preparation of Ethyl 4-amino-6-((16-((6-(methoxycarbonyl)pyridin-2-yl)methyl)-1,4,10,13-tetraoxa-7,16-diazacyclooctadecan-7-yl)methyl)picolinate (10)

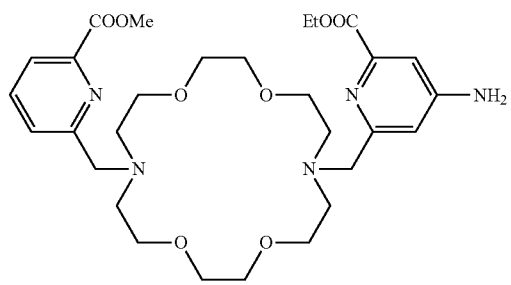

Into a round-bottom flask equipped with a condenser and drying tube were added 9 (0.4210 g, 0.64 mmol), Na$_2$CO$_3$ (0.3400 g, 3.2 mmol), and dry ACN (10 mL). The pale-yellow suspension was heated to reflux over 15 min, after which 6 (0.1508 g, 0.70 mmol, corrected for residual ethyl acetate) was added as a slight suspension in dry ACN (3.5 mL). The mixture was heated at reflux for 44 h and then filtered. The orange filtrate was concentrated at 60° C. under reduced pressure to an orange-brown oil (0.612 g), which was used in the next step without further purification. HRMS (m/z): 590.32021 [M+H]$^+$; Calc: 590.31844.

Preparation of 4-Amino-6-((16-((6-carboxypyridin-2-yl)methyl)-1,4,10,13-tetraoxa-7,16-diazacyclooctadecan-7-yl)methyl)picolinic acid (11.4TFA)

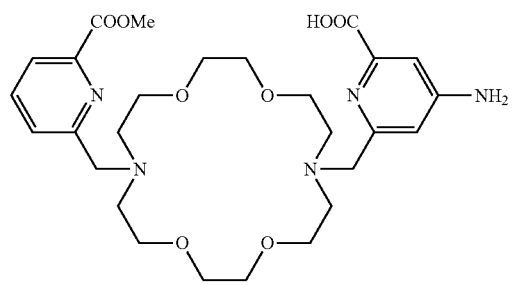

Compound 10 (0.612 g) was dissolved in 6 M HCl (7 mL) and heated at 90° C. for 17 h. The orange-brown solution containing slight precipitate was concentrated at 60° C. under reduced pressure to a pale-tan solid. To this solid was added 10% MeOH/H$_2$O containing 0.1% TFA (3 mL). The slight suspension was filtered and the filtrate was purified by preparative HPLC using Method A. Pure fractions were combined, concentrated at 60° C. under reduced pressure, and then lyophilized to give 11 as an off-white solid (0.2974 g, 46% yield over 2 steps). $^1$H NMR (500 MHz, DMSO-d$_6$) δ=8.13-8.08 (m, 2H), 7.80 (dd, J=7.3, 1.6 Hz, 1H), 7.64 (br s), 7.24 (d, J=2.3 Hz, 1H), 6.76 (d, J=2.3 Hz, 1H), 4.74 (s, 2H), 4.15 (s, 2H), 3.85 (t, J=5.0 Hz, 4H), 3.63 (t, J=5.1 Hz, 4H), 3.57-3.50 (m, 12H), 3.09 (br t, J=5.2 Hz, 4H). $^{13}$C{H} NMR (126 MHz, DMSO-d$_6$) δ 165.96, 163.37, 159.47, 158.78-157.98 (q, TFA), 151.93, 151.64, 148.25, 144.68, 139.59, 128.43, 124.96, 120.79-113.68 (q, TFA), 109.40, 108.96, 70.03, 69.89, 67.09, 65.16, 57.28, 55.85, 54.47, 53.81. $^{19}$F NMR (470 MHz, DMSO-d$_6$) δ=−74.03. EA Found: C, 40.60; H, 4.29; N, 7.04. Calc. for C$_{26}$H$_{37}$N$_5$O$_8$.4CF$_3$COOH: C, 40.69; H, 4.12; N, 6.98. IR (cm$^{-1}$): 3387, 3161, 1735, 1670, 1204, 1130, 791, 722. HPLC t$_R$=11.974 min (Method B); 11.546 min (Method D). HRMS (m/z): 548.26883 [M+H]$^+$; Calc: 548.27149.

Preparation of 6-((16-((6-carboxypyridin-2-yl)methyl)-1,4,10,13-tetraoxa-7,16-diazacyclooctadecan-7-yl)methyl)-4-isothiocyanatopicolinic acid (12, macropa-NCS)

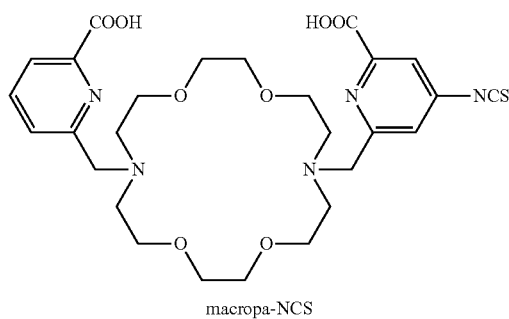

macropa-NCS

A white suspension of 11 (0.1598 g, 0.16 mmol) and $Na_2CO_3$ (0.2540 g, 2.4 mmol) was heated at reflux in acetone (10 mL) for 30 min before the slow addition of $CSCl_2$ (305 μL of $CSCl_2$, 85%, Acros Organics). The resulting orange suspension was heated at reflux for 3 h and then concentrated at 30° C. under reduced pressure to a pale-orange solid. The solid was dissolved portionwise in 10% ACN/$H_2O$ containing 0.2% TFA (8 mL total), filtered, and immediately purified by preparative HPLC using Method C.[108] Pure fractions were combined, concentrated at RT under reduced pressure to remove the organic solvent, and then lyophilized. Fractions that were not able to be concentrated immediately were frozen at −80° C. Isothiocyanate 12 was obtained as a mixture of white and pale-yellow solid (0.0547 g) and was stored at −80° C. in a jar of Drierite. Calculations from $^1H$ NMR and $^{19}F$ NMR spectra of a sample of 12 spiked with a known concentration of fluorobenzene estimated that 12 was isolated as a tetra-TFA salt. $^1H$ NMR (400 MHz, DMSO-$d_6$) δ=8.17-8.06 (m, 2H), 8.00 (s w/fine splitting, 1H), 7.84 (d, J=1.5 Hz, 1H), 7.81-7.75 (d w/fine splitting, J=7.16 Hz, 1H), 4.71 (s, 2H), 4.64 (s, 2H), 3.89-3.79 (m, 8H), 3.62-3.46 (m, 16H). $^{19}F$ NMR (470 MHz, DMSO-$d_6$) δ=−74.17. IR ($cm^{-1}$): ~3500-2800, 2083, 2026, 1735, 1670, 1591, 1448, 1183, 1130, 796, 717. HPLC $t_R$=15.053 min (Method B); 13.885 min (Method D). HRMS (m/z): 590.22600 $[M+H]^+$; Calc: 590.22791.

Preparation of 6-((16-((6-carboxypyridin-2-yl)methyl)-1,4,10,13-tetraoxa-7,16-diazacyclooctadecan-7-yl)methyl)-4-(3-methylthioureido)picolinic acid (13, macropa-NHC(S)NHCH₃)

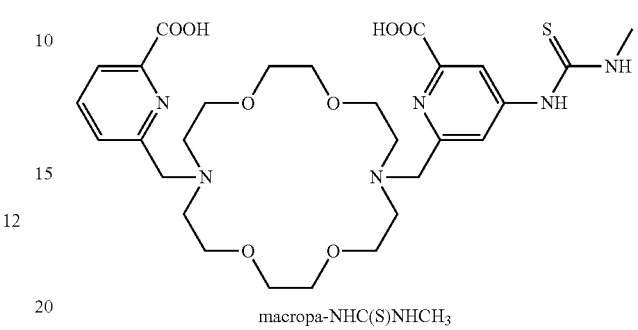

macropa-NHC(S)NHCH₃

Compound 12 was prepared as described above using 0.0873 g (0.087 mmol) of 11, except the purification step was omitted. Instead, directly to the crude solid was added 2 M methylamine in THF (4 mL). The tan-orange suspension was stirred at RT for 2 h and then concentrated at RT under reduced pressure to a pale-peach solid. The solid was dissolved in 10% ACN/$H_2O$ containing 0.2% TFA (2 mL), filtered, and purified by preparative HPLC using Method C. Pure fractions were combined, concentrated at 50° C. under reduced pressure to remove the organic solvent, and then lyophilized. The dark-gold, slightly sticky solid was then recrystallized from ACN with $Et_2O$. The suspension was centrifuged, and the pellet was washed with $Et_2O$ (2×1.5 mL) and dried in vacuo to give 13 as a tan powder (0.0166 g, 22% unoptimized yield from 11). $^1H$ NMR (600 MHz, DMSO-$d_6$) δ=10.56 (s, 1H), 8.64 (br s, 1H), 8.26 (s, 1H), 8.16 (s, 1H), 8.13-8.02 (m, 2H), 7.81-7.73 (d, J=7.40 Hz, 1H), 4.74-4.48 (m, 4H), 3.82 (br s, 8H), 3.57 (br s, 8H), 3.54-3.25 (m, 8H), 2.97 (d, J=4.4 Hz, 4H). $^{13}C\{^1H\}$ NMR (126 MHz, DMSO-$d_6$) δ 180.71, 165.44, 165.39, 158.77-157.95 (q, TFA), 151.04, 150.96, 149.79, 147.95, 147.71, 139.22, 127.76, 124.55, 119.68-112.66 (q, TFA), 116.45, 114.85, 69.36, 64.52, 64.50, 57.00, 56.75, 53.42, 53.37, 31.02. $^{19}F$ NMR (470 MHz, DMSO-$d_6$) δ=−74.49. EA Found: C, 44.66; H, 5.36; N, 9.83. Calc. for $C_{28}H_{40}N_6O_8S \cdot 2CF_3COOH \cdot 1H_2O$: C, 44.34; H, 5.12; N, 9.70. HPLC $t_R$=14.067 min (Method B). HRMS (m/z): 621.26799 $[M+H]^+$; Calc: 621.27011.

X-Ray Diffraction Studies. Single crystals of $H_2macropa \cdot 2HCl \cdot 4H_2O$ suitable for x-ray diffraction were grown from a saturated $H_2O$:acetone (1:5) solution upon standing at room temperature. Single crystals of [La(Hmacropa)($H_2O$)]·($ClO_4$)$_2$ were grown via vapor diffusion of THF into an aqueous solution made acidic (pH ~2) upon addition of the complex. Single crystals of [Lu(macropa)]·$ClO_4$·DMF were grown via vapor diffusion of $Et_2O$ into a DMF solution of the complex.

X-ray diffraction data for $H_2macropa \cdot 2HCl \cdot 4H_2O$, [La(Hmacropa)($H_2O$)]·($ClO_4$)$_2$, and [Lu(macropa)]·$ClO_4$·DMF were collected on a Bruker APEX 2 CCD Kappa diffractometer (Mo Kα, λ=0.71073 Å) at 223 K. The structures were solved through intrinsic phasing using SHELXT[109] and refined against $F^2$ on all data by full-matrix least squares with SHELXL[110] following established refinement strategies.[111] All non-hydrogen atoms were refined anisotropically. Hydrogen atoms were included in the model at geometrically calculated positions and refined using a riding model. Hydrogen atoms bound to nitrogen and oxygen were located in the difference Fourier synthesis and subsequently refined semi-freely with the help of distance restraints. The isotropic displacement parameters of all hydrogen atoms were fixed to 1.2 times the U value of the atoms they are linked to (1.5 times for methyl groups). For [La(Hmacropa)(H$_2$O)].(ClO$_4$)$_2$, a partially occupied solvent molecule of water was included in the unit cell but could not be satisfactorily modeled. Therefore, that solvent was treated as a diffuse contribution to the overall scattering without using specific atom positions by the solvent masking function in Olex2.[112]

La$^{3+}$ and Lu$^{3+}$ Titrations with Macropa. The pH of a 10 mM 3-(N-morpholino)propanesulfonic acid (MOPS) buffer was adjusted to 7.4 using aqueous NMe$_4$OH. The ionic strength was set at 100 mM using NMe$_4$Cl. Stock solutions of LaCl$_3$.6.8H$_2$O (40 mM) and LuCl$_3$.6H$_2$O (21 mM) were prepared in 1 mM HCl. A stock solution of H$_2$macropa.2HCl.4H$_2$O (8.8 mM) was prepared in MOPS buffer. From these stock solutions, titration solutions containing macropa (100 μM) and either LaCl$_3$ or LuCl$_3$ were prepared in MOPS. Each metal ion titration was carried out at RT by adding 5-10 μL aliquots of titrant to a cuvette containing 3000 μL of macropa (100 μM) in MOPS. Each sample was allowed to equilibrate for 5 min following every addition before a spectrum was acquired. Complexation of the metal ion was monitored by the decrease in absorbance at 268 nm, the $\lambda_{max}$ of macropa. Titrant was added until no further spectral changes were detected.

Kinetic Inertness of La$^{3+}$ and La$^{3+}$ Complexes of Macropa: Transchelation Challenge. A stock solution of ethylenediaminetetraacetic acid (EDTA, 100 mM) was made in MOPS buffer (prepared as described above) by adjusting the pH of the initial suspension to 6.6 using aqueous NMe$_4$OH. A stock solution of diethylenetriaminepentaacetic acid (DTPA, 125 mM) was prepared in H$_2$O by adjusting the pH to 7.4 as described for EDTA. This solution was serially diluted with H$_2$O to yield 12.5 mM and 1.25 mM solutions of DTPA.

The preformed La$^{3+}$ and Lu$^{3+}$ complexes of macropa were challenged with EDTA. Challenges were initiated by adding an aliquot of solution containing EDTA (98.7 mM) and macropa (100 μM) in MOPS buffer to each solution of complex. The final ratios of M:macropa:EDTA were approximately 1:1:20 (La) and 1:1:10 (Lu). Solutions were repeatedly analyzed by UV spectroscopy over the course of 21 days for any spectral changes. The final pH of each solution was between 7.18 and 7.25.

The complex formed in situ between La$^{3+}$ and macropa was more rigorously challenged with excess DTPA. A solution containing 500 μM of complex, prepared using the LaCl$_3$ and macropa stock solutions described above, was left to equilibrate for 5 min. Subsequently, it was portioned into cuvettes and diluted with either 125 mM DTPA, 12.5 mM DTPA, 1.25 mM DTPA, or MOPS to yield solutions containing 1000-, 100-, 10-, or 0-fold excess DTPA and 100 μM concentration of macropa. These solutions were repeatedly analyzed by UV spectroscopy over the course of 21 days for any spectral changes. The final pH of each solution was between 7.11 and 7.42.

$^{225}$Ac Radiolabeling of Macropa and DOTA

General. $^{225}$Ac and $^{225}$Ra were produced by the spallation of uranium carbide, separated downstream from other radionuclides by a mass separator using the Isotope Separator and Accelerator (ISAC) isotope separation on-line (ISOL) facility at TRIUMF (Vancouver, BC, Canada), and were collected via literature protocols.[103,104] $^{225}$Ac was then separated from $^{225}$Ra via DGA column[105,106] (branched, 50-100 Eichrom Technologies LLC) and obtained in 0.05 M HNO$_3$ for use in radiolabeling experiments. Aluminum-backed TLC plates (silica gel 60, F$_{254}$, EMD Millipore, Darmstadt, Germany) were used to analyze $^{225}$Ac radiolabeling reaction progress. Instant thin layer chromatography paper impregnated with silica gel (iTLC-SG, Agilent Technologies, Mississauga, ON, Canada) was used in La$^{3+}$ and serum stability challenges. TLC plates were developed and then counted on a BioScan System 200 imaging scanner equipped with a BioScan Autochanger 1000 and WinScan software at least 8 h later to allow time for daughter isotopes to decay completely, ensuring that the radioactive signal measured was generated by parent $^{225}$Ac. Quantitative radioactivity measurements of $^{225}$Ac, $^{221}$Fr, and $^{213}$Bi were determined via gamma-spectroscopy using a high-purity germanium (HPGe) detector (Canberra GR1520, Meriden, Conn.) calibrated using a NIST-traceable mixed $^{133}$Ba and $^{152}$Eu source. Detector dead time was maintained below 10% for all measurements. Data was analyzed using Genie 2000 software (v3.4, Canberra, Meriden, Conn.).

Concentration Dependence. Various concentrations of macropa and DOTA were radiolabeled with $^{225}$Ac$^{3+}$ to determine the lowest concentration at which >95% radiolabeling still occurred. Stock solutions of H$_2$macropa.2HCl.4H$_2$O (10$^{-3}$-10$^{-8}$ M) and H$_4$DOTA (10$^{-3}$, 10$^{-5}$, and 10$^{-7}$ M) were prepared in H$_2$O. For each radiolabeling reaction, ligand (10 μL) and $^{225}$Ac (10-26 kBq, 10-30 μL) were sequentially added to NH$_4$OAc buffer (pH 6, 0.15 M, 150 μL) to give final ligand concentrations of 5.3×10$^{-5}$-5.9×10$^{-10}$ M for macropa and 5.9×10$^{-5}$-5.9×10$^{-9}$ M for DOTA. The final pH of all labeling reactions was between 5.5 and 6. The reaction solutions were maintained at ambient temperature or 80° C. Reaction progress was monitored at 5 and 30 min by spotting 3-5 μL it of the reaction solution onto TLC plates. The plates were developed with a mobile phase of 0.4 M sodium citrate (pH 4) containing 10% MeOH and then counted. Under these conditions, [$^{225}$Ac(macropa)]$^+$ and [$^{225}$Ac(DOTA)]$^-$ remained at the baseline (R$_F$=0) and any unchelated $^{225}$Ac ($^{225}$Ac-citrate) migrated with the solvent front (R$_F$=1). Radiochemical yields (RCYs) were calculated by integrating area under the peaks on the radiochromatogram and dividing the counts associated with the $^{225}$Ac-complex (R$_F$=0) by the total counts integrated along the length of the TLC plate.

Kinetic Inertness of $^{225}$Ac Complexes of Macropa and DOTA.

General. Stock solutions of La(NO$_3$)$_3$ (0.001 M or 0.1 M) were prepared in H$_2$O. To the radiolabeled samples containing macropa (10 μL of 10$^{-5}$ M stock; 1.0×10$^{-10}$ moles) or DOTA (10 μL of 10$^{-3}$ M stock; 1.0×10$^{-8}$ moles) and $^{225}$Ac (10 μL, 26 kBq) in NH$_4$OAc buffer (pH 6, 0.15 M, 150 μL), a 50-fold mole excess of La$^{3+}$ was added (5 μL of 0.001 M or 0.1 M stock were added to solutions containing macropa and DOTA, respectively). The solutions were kept at room temperature and analyzed by iTLC at several time points over the course of 8 days. The iTLC plates were developed using citric acid (0.05 M, pH 5) as the eluent. Under these conditions, [$^{225}$Ac(macropa)]$^+$ and [$^{225}$Ac(DOTA)]$^-$ remained at the baseline (R$_F$=0) and any unchelated $^{225}$Ac ($^{225}$Ac-citrate) migrated with the solvent front (R$_F$=1). Percent of complex remaining intact was calculated by integrating area under the peaks on the radiochromatogram and dividing the counts associated with the $^{225}$Ac-complex ($R_F$=0) by the total counts integrated along the length of the iTLC plate.

Transmetalation by La$^{3+}$. [$^{225}$Ac(macropa)]$^+$ and [$^{225}$Ac(DOTA)]$^-$ were prepared using 10$^{-5}$ M and 10$^{-3}$ M stock solutions (10 μL) of macropa and DOTA, respectively, to give final ligand concentrations of 5.9×10$^{-7}$ M (macropa) and 5.9×10$^{-5}$ M (DOTA). After confirming a radiochemical yield of >90% by TLC using 0.4 M sodium citrate (pH 4) containing 10% MeOH as the mobile phase, 160 μL of human serum (an equal volume based on labeling reaction volume) were added to each radiolabeled solution. A control solution was also prepared in which water was substituted for ligand. The solutions were monitored over the course of 8 days by iTLC. The plates were developed with EDTA (50 mM, pH 5) as the eluent. Under these conditions, [$^{225}$Ac(macropa)]$^+$ and [$^{225}$Ac(DOTA)]$^-$ complexes remained at the baseline ($R_F$=0) and any $^{225}$Ac ($^{225}$Ac-EDTA) that had been transchelated by serum migrated with the solvent front ($R_F$=1). Percent of complex remaining intact was calculated.

In Vivo Biodistribution of $^{225}$Ac Complexes of Macropa and DOTA. All experiments were approved by the Institutional Animal Care Committee (IACC) of the University of British Columbia and were performed in accordance with the Canadian Council on Animal Care Guidelines. A total of 9 female C57BL/6 mice (6-8 weeks old, 20-25 g) were used for the biodistribution study of each radiometal complex, n=3 for each time point.

Macropa (100 μL of a 1 mg/mL solution in NH$_4$OAc) was diluted with 387 μL of NH$_4$OAc (1 M, pH 7), and an aliquot (203 μL) of $^{225}$Ac(NO$_3$)$_3$ (~157 kBq) was then added; the pH of this solution was adjusted to 6.5-7 by the addition of 1 M NaOH (210 μL, trace metal grade). After 5 min at ambient temperature, the reaction solution was analyzed by TLC (0.4 M pH 4 sodium citrate as the eluent), which confirmed >95% radiochemical yield. The reaction was allowed to proceed overnight, and the radiochemical yield was again confirmed to be >95% the following morning. At this time, mice were anesthetized by 2% isoflurane, and approximately 100 μL (10-15 kBq) of the [$^{225}$Ac(macropa)]$^+$ complex were injected into the tail vein of each mouse. After injection, mice were allowed to recover and roam freely in their cages, and were euthanized by CO$_2$ inhalation at 15 min, 1 h, or 5 h (n=3 at each time point) post-injection. Blood was collected by cardiac puncture and placed into an appropriate test tube for scintillation counting. Tissues collected included heart, liver, kidneys, lungs, small intestine, large intestine, brain, bladder, spleen, stomach, pancreas, bone, thyroid, tail, urine, and feces. Tissues were weighed and then counted with a calibrated gamma counter (Packard, Cobra II model 5002) using three energy windows: 60-120 keV (window A), 180-260 keV (window B), and 400-480 keV (window C). Counting was performed both immediately after sacrifice and after 7 days; counts were decay corrected from the time of injection and then converted to the percentage of injected dose (% ID) per gram of tissue (% ID/g). No differences were noted between the data; therefore, the biodistributions are reported using the data acquired immediately using window A.

The biodistribution studies of [$^{225}$Ac(DOTA)]$^-$ and $^{225}$Ac(NO$_3$)$_3$ were carried out as described above for [$^{225}$Ac(macropa)]$^+$, with the following modifications. [$^{225}$Ac(DOTA)]$^-$ was prepared by adding $^{225}$Ac(NO$_3$)$_3$ (338 μL, 1.1 MBq) to a solution of DOTA (100 μg, 20 mg/mL in H$_2$O) in NH$_4$OAc (467 μL, 0.15 M, pH 7). The pH of the solution was adjusted to 7 using NH$_4$OAc (150 μL, 1 M, pH 7) and the solution was heated at 85° C. for 45 min. RCY>99% was confirmed by TLC as described above. [$^{225}$Ac(DOTA)]$^-$ was diluted with saline to a final concentration of 0.05 MBq/100 μL, and 100 μL were injected into each mouse. $^{225}$Ac(NO$_3$)$_3$ (~58 μL, 0.4 MBq) was diluted and injected in the same manner as [$^{225}$Ac(DOTA)]$^-$. One mouse that was to be euthanized at the 5 h time point in the [$^{225}$Ac(DOTA)]$^-$ study died shortly after injection. In the same manner, one mouse that was to be euthanized at the 1 h time point in the $^{225}$Ac(NO$_3$)$_3$ study died.

Hydrolysis of Macropa-NCS and p-SCN-Bn-DOTA. To screw-capped vials containing approximately 1 mg of macropa-NCS (compound 12, n=4) or p-SCN-Bn-DOTA (n=5) was added 1 mL of 0.1 M pH 9.1 NaHCO$_3$ buffer containing 0.154 M NaCl, which had been passed through a column of pre-equilibrated Chelex. After stirring for 1 min, each solution was filtered through a 0.2 μm PES or PTFE membrane. Five μL aliquots were removed from the vials at various time points over the course of 46-72 h and analyzed by HPLC. Method D was employed for macropa-NCS. Method B was employed for p-SCN-Bn-DOTA using an Epic Polar C18 column, 120 Å, 10 μm, 25 cm×4.6 mm (ES Industries, West Berlin, N.J.) at a flow rate of 1 mL/min. Between samplings, the vials were stored at room temperature (23±1° C.) away from light. Hydrolysis was considered complete once the peak at 13.8 min (corresponding to 12) or 18.417 min (corresponding to p-SCN-Bn-DOTA) had disappeared or had negligible integration. A linear regression performed on the plots of ln peak area versus time provided the pseudo-first order rate constant ($k_{obs}$) as the negative slope. The half-life ($t_{1/2}$) was calculated using the equation $t_{1/2}$=0.693/$k_{obs}$. The half-life of each compound is reported as the mean±1 standard deviation.

Titration of Macropa-NHC(S)NHCH$_3$ Conjugate with La$^{3+}$. The titration of the macropa-NHC(S)NHCH$_3$ conjugate (13) with La$^{3+}$ was carried out at pH 7.4 for macropa, except that the stock solution of 13 (0.760 mM) was prepared in ACN instead of MOPS. The amount of ACN in the sample did not exceed 3.3% by volume. A wait time of 3 min after the addition of each aliquot was found to be sufficient for the sample to reach equilibrium before spectral acquisition. Complexation of the metal ion was monitored using the increase in absorbance at 300 nm. The pH of the solution at the end of the titration was 7.43.

Kinetic Inertness of La-Macropa-NHC(S)NHCH$_3$: Transchelation Challenge. Solutions of diethylenetriaminepentaacetic acid (DTPA; 125 mM and 12.5 mM) were prepared in MOPS buffer (pH 7.4). A MOPS solution containing macropa-NHC(S)NHCH$_3$ (126.7 μM, 16.7% ACN by volume) and LaCl$_3$ (126.2 μM) was prepared using the stock solutions described above and was left to equilibrate for 10 min. Subsequently, it was portioned into cuvettes and diluted with either 125 mM DTPA, 12.5 mM DTPA, or MOPS to yield solutions containing 1000-, 100-, or 0-fold excess DTPA. The final concentration of macropa-NHC(S)NHCH$_3$ in each cuvette was 25.3 μM. These solutions were repeatedly analyzed by UV spectrophotometry over the course of 21 days for any spectral changes. The final pH of each solution was between 7.42 and 7.49. The experiment was performed in triplicate.

Conjugation of Macropa-NCS and p-SCN-Bn DOTA to Trastuzumab.

General. All glassware was washed overnight in 1M HCl. Saline (0.154 M NaCl) and all buffer solutions were passed through a column of Chelex-100 pre-equilibrated with the appropriate buffer. Trastuzumab (Tmab, Genentech) was purified using a Zeba spin desalting column (2 mL or 5 mL, 40 MWCO, Thermo Scientific, Waltham, Mass.) according to the manufacturer's protocol, with saline as the mobile phase. The concentration of purified Tmab was calculated via the Beer-Lambert law using $A_{280}$ and an $\varepsilon_{280}$ of 1.446 mL mg$^{-1}$ cm$^{-1}$.[107] Purified Tmab and Tmab conjugates were stored at 4° C.

Conjugation of Macropa-NCS to Tmab. A stock solution containing 4.4 mg/mL of macropa-NCS (12) was prepared in 0.1 M pH 9.1 NaHCO$_3$ buffer containing 0.154 M NaCl and was stored at −80° C. The stability of 12 during storage was verified by analytical HPLC. To a portion of Tmab in saline (74 μL) were added 12 (52 μL) and NaHCO$_3$ buffer (266 μL), so that the final concentrations of Tmab and 12 were 5.1 mg/mL and 0.59 mg/mL, respectively. Macropa-NCS was estimated to be in 16-fold molar excess to Tmab based on a molecular weight of 1045.76 g/mol for 12 (tetra-TFA salt). The pH of this solution was between 8 and 9 by litmus paper. The solution was rocked gently at room temperature for 17.5 h and then purified using a spin column.

Conjugation of p-NCS-Bn-DOTA to Tmab. A stock solution containing 3.05 mg/mL of p-NCS-Bn-DOTA was prepared in H$_2$O and stored at −80° C. To a portion of Tmab in saline (66 μL) were added p-NCS-Bn-DOTA (49 μL) and NaHCO$_3$ buffer (274.5 μL), so that the final concentrations of Tmab and p-NCS-Bn-DOTA were 5.1 mg/mL and 0.38 mg/mL (16-fold molar excess of L), respectively. The pH of this solution was between 8 and 9 by litmus paper. The solution was rocked gently at room temperature for 17.5 h and then purified using a spin column.

Determination of Conjugate Protein Concentration by BCA Assay. The concentration of protein in macropa-Tmab and DOTA-Tmab conjugates was determined using the Pierce™ BCA Protein Assay kit (Thermo Scientific, Waltham, Mass., microplate protocol). Tmab was employed as the protein standard. A stock solution of purified Tmab was diluted with saline and the concentration of this solution (1.83 mg/mL) was determined using a NanoDrop 1000 Spectrophotometer (Thermo Scientific, Waltham, Mass.). The standard curve was linear ($r^2$=0.9966) over the concentration range measured (0-1828 μg/mL). The protein concentration of each conjugate was calculated from two independent dilutions, each measured in triplicate, and the results were averaged to give a protein concentration of 4.557 mg/mL for macropa-Tmab and 2.839 mg/mL for DOTA-Tmab.

Ligand-to-Protein Ratio Analysis by MALDI-ToF. The average number of macropa or DOTA ligands conjugated to Tmab was determined by MALDI-ToF MS/MS on a Bruker autoflex speed at the Alberta Proteomics and Mass Spectrometry Facility (University of Alberta, Canada) using a procedure described elsewhere.[108] Purified Tmab and the conjugates were analyzed in duplicate, and the [M+H]$^+$ mass signals from the chromatograms were averaged for each compound. The ligand-to-protein (L:P) ratio for each conjugate was obtained by subtracting the molecular weight of Tmab from the molecular weight of the conjugate, and subsequently dividing by the mass of the bifunctional ligand.

$^{225}$Ac Radiolabeling of Tmab Conjugates and Serum Stability of Complexes.

General. Instant thin layer chromatography paper impregnated with silica gel (iTLC-SG, Agilent Technologies, Mississauga, ON, Canada) was used to monitor the progress of $^{225}$Ac radiolabeling reactions and to determine serum stability. TLC plates were developed as described below and then counted on a BioScan System 200 imaging scanner equipped with a BioScan Autochanger 1000 and WinScan software at least 8 h later to allow time for daughter isotopes to decay completely, ensuring that the radioactive signal measured was generated by parent $^{225}$Ac.

$^{225}$Ac Radiolabeling Studies. In a total reaction volume of 200 μL made up with NH$_4$OAc buffer (pH 6, 0.15 M), $^{225}$Ac (10 or 20 kBq, 7-10 μL) was mixed with 25-100 μg of either macropa-Tmab (5.5-22 μL) or DOTA-Tmab (8.81-35.2 μL), and the pH was adjusted to 5 with NaOH. A control solution was also prepared in which unmodified Tmab (25 μg) was substituted in place of conjugate. The reaction solutions were maintained at ambient temperature and analyzed at 5 min, 30 min, 1 h, 2 h, 3 h, and 4 h by spotting 8 μL in triplicate on iTLC strips. The strips were developed with a mobile phase of 0.05 M citric acid (pH 5). Under these conditions, $^{225}$Ac-macropa-Tmab and $^{225}$Ac-DOTA-Tmab remained at the baseline of the plate ($R_F$=0) and any unchelated $^{225}$Ac ($^{225}$Ac-citrate) migrated with the solvent front ($R_F$=1). Radiochemical yields (RCYs) were calculated by integrating area under the peaks on the radiochromatogram and dividing the counts associated with the $^{225}$Ac-complex ($R_F$=0) by the total counts integrated along the length of the TLC plate.

Stability of $^{225}$Ac-macropa-Tmab in Human Serum. A solution of $^{225}$Ac-macropa-Tmab was prepared using 100 μg of protein. After confirmation by TLC that a RCY of >95% had been achieved, human serum was thawed to room temperature and added to the radiolabeled immunoconjugate to give a solution containing 90% serum by volume. The sample was incubated at 37° C. At various time points over the course of 7 days, aliquots (15-30 μL) were removed from the sample and spotted in triplicate onto iTLC strips. The strips were developed using an EDTA (50 mM, pH 5.2) mobile phase and counted. Under these conditions, $^{225}$Ac-macropa-Tmab remained at the baseline ($R_F$=0) and any $^{225}$Ac ($^{225}$Ac-EDTA) that had been transchelated by serum migrated with the solvent front ($R_F$=1). Percent of complex remaining intact was calculated.

As an additional challenge, separate aliquots (39 μL) were also removed from the serum sample on days 1 and 7 and mixed with 50 mM DTPA (pH 7, 13 μL) to challenge off any $^{225}$Ac that was only loosely bound by the radioimmunoconjugate. After incubation of this solution at 37° C. for 15 minutes, an aliquot (30 μL) was spotted in triplicate on iTLC plates and developed using an EDTA (50 mM, pH 5.2) mobile phase. Percent of complex remaining intact was calculated.

In Vivo Biodistribution Studies of [$^{225}$Ac(macropa)]$^+$, [$^{225}$Ac(DOTA)]$^-$, and $^{225}$Ac(NO$_3$)$_3$

TABLE 1

Organ distribution of $^{225}$Ac complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window A (60-120 keV).

| Organ | 15 min | SD | 1 h | SD | 5 h | SD |
|---|---|---|---|---|---|---|
| \[$^{225}$Ac(macropa)\]$^+$ | | | | | | |
| blood | 5.11 | 2.82 | 0.40 | 0.38 | 0.01 | 0.01 |
| urine | 1378.82 | 971.53 | 489.11 | 26.75 | 12.78 | 6.10 |
| feces | 0.91 | 1.18 | 0.28 | 0.14 | 3.46 | 1.06 |
| heart | 2.19 | 0.60 | 0.31 | 0.24 | 0.10 | 0.11 |
| liver | 2.28 | 0.41 | 0.75 | 0.18 | 0.39 | 0.03 |
| kidneys | 27.55 | 7.51 | 13.36 | 17.13 | 0.74 | 0.06 |
| lungs | 5.98 | 1.81 | 0.51 | 0.36 | 0.01 | 0.04 |
| small intestines | 2.64 | 1.08 | 1.10 | 0.47 | 0.29 | 0.20 |
| large intestines | 2.40 | 0.52 | 0.36 | 0.10 | 0.49 | 0.22 |
| brain | 0.26 | 0.09 | 0.12 | 0.07 | 0.02 | 0.02 |
| bladder | 46.74 | 24.65 | 6.23 | 7.44 | 4.25 | 5.27 |
| spleen | 2.52 | 1.08 | 0.51 | 0.19 | 0.11 | 0.03 |
| stomach | 2.97 | 0.72 | 0.41 | 0.08 | 0.01 | 0.06 |
| pancreas | 1.46 | 0.64 | 0.19 | 0.16 | 0.10 | 0.06 |
| bone (femur + joint) | 2.52 | 0.34 | 0.31 | 0.16 | 0.05 | 0.10 |
| thyroids | 28.23 | 17.90 | 3.18 | 2.21 | 0.10 | 7.95 |
| tail | 8.84 | 1.56 | 1.82 | 1.11 | 0.14 | 0.09 |
| \[$^{225}$Ac(DOTA)\]$^-$ | | | | | | |
| blood | 5.2881 | 2.9807 | 0.1144 | 0.0203 | 0.0140 | 0.0024 |
| urine | 1467.9186 | 1073.9229 | 158.6102 | 141.1945 | 1.1612 | 0.3653 |
| feces | 6.2730 | 8.7284 | 0.2035 | 0.2433 | 5.5318 | 1.7685 |
| heart | 2.3335 | 0.7337 | 0.1012 | 0.0853 | 0.0664 | 0.0091 |
| liver | 2.2520 | 0.5051 | 0.2715 | 0.1973 | 0.1010 | 0.0063 |
| kidneys | 27.6566 | 6.8974 | 1.4020 | 0.2124 | 0.6172 | 0.0168 |
| lungs | 5.7556 | 1.7234 | 0.1555 | 0.0800 | 0.0390 | 0.0135 |
| small intestines | 2.6370 | 1.3350 | 1.7207 | 2.1165 | 0.0967 | 0.0232 |
| large intestines | 2.3348 | 0.7436 | 0.1229 | 0.0551 | 0.2026 | 0.1073 |
| brain | 0.2655 | 0.0598 | 0.0224 | 0.0123 | 0.0213 | 0.0021 |
| bladder | 48.2703 | 26.4988 | 4.7351 | 4.9621 | 0.3551 | 0.0335 |
| spleen | 2.5905 | 1.3909 | 0.0938 | 0.0322 | 0.1380 | 0.0733 |
| stomach | 2.7440 | 0.8312 | 0.1367 | 0.1078 | 0.0852 | 0.0100 |
| pancreas | 1.5090 | 0.6828 | 0.0743 | 0.0752 | 0.0677 | 0.0090 |
| bone (femur + joint) | 2.6298 | 0.6802 | 0.4487 | 0.0586 | 0.2063 | 0.0231 |
| thyroids | −5.7725 | 27.0550 | 2.3564 | 2.7015 | 3.6425 | 1.8897 |
| tail | 8.8606 | 1.1879 | 0.8091 | 0.1272 | 0.3057 | 0.0766 |
| $^{225}$Ac(NO$_3$)$_3$ | | | | | | |
| blood | 40.966 | 6.455 | 20.8234 | 0.8102 | 1.9886 | 0.5457 |
| urine | 5.527 | 3.460 | 4.5194 | 0.4803 | 4.8267 | 3.6549 |
| feces | 0.240 | 0.070 | 0.2189 | 0.1167 | 0.9445 | 0.7998 |
| heart | 8.557 | 2.698 | 4.4261 | 1.2771 | 1.3450 | 0.2326 |
| liver | 22.899 | 1.788 | 39.8269 | 4.5062 | 59.8156 | 10.4928 |
| kidneys | 10.468 | 1.897 | 7.2170 | 1.5026 | 4.6910 | 2.3005 |
| lungs | 12.757 | 2.883 | 8.2412 | 1.9189 | 4.1871 | 3.8011 |
| small intestines | 2.002 | 0.094 | 1.5594 | 0.3191 | 1.3704 | 0.4345 |
| large intestines | 1.116 | 0.145 | 0.6035 | 0.4502 | 0.6479 | 0.2782 |
| brain | 0.614 | 0.283 | 0.2995 | 0.0893 | 0.0452 | 0.0343 |
| bladder | 1.477 | 0.689 | 0.9047 | 0.0759 | 1.4947 | 2.4402 |
| spleen | 22.733 | 4.962 | 34.8831 | 1.6768 | 62.9614 | 12.7041 |

TABLE 1-continued

Organ distribution of $^{225}$Ac complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window A (60-120 keV).

| Organ | 15 min | SD | 1 h | SD | 5 h | SD |
|---|---|---|---|---|---|---|
| stomach | 2.348 | 0.250 | 1.6211 | 0.0147 | 2.6131 | 1.4450 |
| pancreas | 2.366 | 0.922 | 2.1771 | 0.8907 | 0.4874 | 0.4300 |
| bone (femur + joint) | 2.764 | 0.757 | 2.4707 | 0.1198 | 3.5460 | 0.6374 |
| thyroids | 4.391 | 1.511 | 2.5988 | 4.9499 | −2.7052 | 2.9758 |
| tail | 7.459 | 5.674 | 5.7939 | 1.8506 | 23.4055 | 19.5704 |

TABLE 2

Organ distribution of $^{225}$AC complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window B (180-260 keV).

| Organ | 15 min | SD | 1 h | SD | 5 h | SD |
|---|---|---|---|---|---|---|
| [$^{225}$Ac(macropa)]$^+$ | | | | | | |
| blood | 5.23 | 2.93 | 0.39 | 0.38 | 0.00 | 0.01 |
| urine | 1541.60 | 1105.98 | 517.19 | 11.65 | 13.51 | 6.04 |
| feces | 1.04 | 0.92 | 0.27 | 0.21 | 3.49 | 1.18 |
| heart | 2.39 | 0.80 | 0.20 | 0.31 | −0.04 | 0.12 |
| liver | 2.17 | 0.40 | 0.70 | 0.16 | 0.36 | 0.01 |
| kidneys | 27.86 | 7.39 | 12.97 | 17.16 | 0.78 | 0.14 |
| lungs | 5.83 | 1.81 | 0.54 | 0.25 | −0.05 | 0.14 |
| small intestines | 2.59 | 1.19 | 0.94 | 0.46 | 0.29 | 0.21 |
| large intestines | 2.53 | 0.57 | 0.22 | 0.18 | 0.45 | 0.27 |
| brain | 0.23 | 0.06 | 0.12 | 0.11 | −0.01 | 0.04 |
| bladder | 47.64 | 25.00 | 5.92 | 8.15 | 3.69 | 6.69 |
| spleen | 2.55 | 1.54 | 0.23 | 0.26 | 0.09 | 0.06 |
| stomach | 3.29 | 1.03 | 0.33 | 0.26 | 0.04 | 0.14 |
| pancreas | 1.63 | 0.73 | 0.12 | 0.22 | −0.12 | 0.16 |
| bone (femur + joint) | 2.69 | 0.63 | 0.17 | 0.11 | 0.02 | 0.01 |
| thyroids | −2.22 | 12.06 | 0.10 | 5.33 | −6.94 | 8.77 |
| tail | 9.39 | 1.59 | 1.82 | 1.04 | 0.13 | 0.05 |
| [$^{225}$Ac(DOTA)]$^-$ | | | | | | |
| blood | 5.6357 | 3.2852 | 0.1127 | 0.0403 | 0.0292 | 0.0172 |
| urine | 1635.4394 | 1233.7980 | 159.1628 | 143.0187 | 3.6967 | 3.3377 |
| feces | 1.0222 | 0.9859 | 0.2349 | 0.2923 | 3.3534 | 1.0198 |
| heart | 2.7276 | 0.7955 | 0.1378 | 0.1197 | 0.0879 | 0.0591 |
| liver | 2.1817 | 0.4921 | 0.2672 | 0.1890 | 0.2712 | 0.2370 |
| kidneys | 28.0858 | 6.9019 | 1.2560 | 0.1319 | 0.6718 | 0.1380 |
| lungs | 6.0147 | 1.8416 | 0.1946 | 0.1077 | 0.1289 | 0.0320 |
| small intestines | 2.5009 | 1.2567 | 1.8809 | 2.3424 | 0.2065 | 0.1617 |
| large intestines | 2.5365 | 0.7142 | 0.0813 | 0.0554 | 0.2527 | 0.1980 |
| brain | 0.2735 | 0.1473 | 0.0248 | 0.0120 | 0.0513 | 0.0110 |
| bladder | 54.4696 | 32.7034 | 4.7141 | 5.1077 | 0.7521 | 0.0884 |
| spleen | 2.9076 | 1.5773 | 0.0825 | 0.0965 | 0.0834 | 0.2219 |
| stomach | 2.7311 | 0.9322 | 0.1379 | 0.1390 | 0.1789 | 0.0565 |
| pancreas | 1.4929 | 1.2189 | 0.0746 | 0.0806 | 0.1266 | 0.0354 |
| bone (femur + joint) | 3.0357 | 0.7199 | 0.4126 | 0.0368 | 0.1478 | 0.1689 |
| thyroids | 1.6601 | 7.1867 | 2.6514 | 6.1376 | 16.2357 | 11.0860 |
| tail | 9.4746 | 1.5429 | 0.8973 | 0.0672 | 0.1634 | 0.0768 |
| $^{225}$Ac(NO$_3$)$_3$ | | | | | | |
| blood | 41.5628 | 6.0720 | 21.4460 | 1.0862 | 2.0018 | 0.5989 |
| urine | 5.0951 | 2.4036 | 7.0564 | 2.0984 | 3.3142 | 2.6426 |
| feces | 0.3857 | 0.1799 | 0.3300 | 0.1741 | 1.0201 | 0.9002 |
| heart | 8.3605 | 2.5149 | 4.5832 | 1.4669 | 1.3948 | 0.3318 |
| liver | 23.6091 | 2.1849 | 41.0995 | 5.1387 | 62.0765 | 10.0091 |

TABLE 2-continued

Organ distribution of $^{225}$Ac complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window B (180-260 keV).

| Organ | 15 min | SD | 1 h | SD | 5 h | SD |
|---|---|---|---|---|---|---|
| kidneys | 9.6424 | 1.6131 | 6.8770 | 1.0099 | 3.8752 | 1.6179 |
| lungs | 12.9714 | 2.7540 | 8.4426 | 1.9117 | 4.3379 | 3.9596 |
| small intestines | 1.9641 | 0.1853 | 1.5192 | 0.2815 | 1.2201 | 0.3708 |
| large intestines | 1.1570 | 0.1960 | 0.5629 | 0.3460 | 0.6744 | 0.2893 |
| brain | 0.6536 | 0.2639 | 0.3247 | 0.0633 | 0.0290 | 0.0219 |
| bladder | 1.6996 | 0.7289 | 0.8092 | 0.2576 | 1.5234 | 2.6761 |
| spleen | 24.0497 | 5.3531 | 37.1540 | 0.1801 | 65.9117 | 13.1934 |
| stomach | 2.3704 | 0.3085 | 1.5867 | 0.2853 | 2.5322 | 1.4903 |
| pancreas | 2.2821 | 0.9761 | 2.1579 | 0.8408 | 0.4455 | 0.3936 |
| bone (femur + joint) | 2.7487 | 0.6608 | 2.7705 | 0.0730 | 3.8533 | 0.7991 |
| thyroids | 9.6295 | 8.0396 | 5.7426 | 3.0938 | −4.6044 | 2.5708 |
| tail | 8.0722 | 6.2766 | 6.4201 | 2.1693 | 25.4744 | 20.7518 |

TABLE 3

Organ distribution of $^{225}$Ac complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window C (400-480 keV).

| Organ | 15 min | SD | 1 h | SD | 5 h | SD |
|---|---|---|---|---|---|---|
| [$^{225}$Ac(macropa)]$^+$ | | | | | | |
| blood | 6.49 | 4.64 | 0.54 | 0.55 | 0.04 | 0.03 |
| urine | 2387.66 | 1987.77 | 641.63 | 49.58 | 22.27 | 8.14 |
| feces | 1.26 | 2.00 | 0.69 | 0.50 | 5.27 | 2.17 |
| heart | 2.87 | 1.51 | 0.23 | 0.97 | 0.28 | 0.84 |
| liver | 2.72 | 0.61 | 1.08 | 0.45 | 0.55 | 0.08 |
| kidneys | 33.46 | 5.62 | 17.38 | 21.12 | 1.07 | 0.37 |
| lungs | 7.55 | 3.24 | 0.84 | 0.62 | 0.15 | 0.14 |
| small intestines | 3.46 | 2.44 | 1.62 | 0.76 | 0.42 | 0.28 |
| large intestines | 3.02 | 1.11 | 0.79 | 0.51 | 0.68 | 0.17 |
| brain | 0.17 | 0.10 | 0.23 | 0.13 | −0.01 | 0.08 |
| bladder | 64.68 | 45.85 | 9.00 | 3.35 | 8.52 | 10.72 |
| spleen | 3.79 | 2.96 | 0.48 | 1.92 | 0.43 | 0.14 |
| stomach | 3.45 | 1.29 | 0.17 | 0.77 | 0.13 | 0.23 |
| pancreas | 3.00 | 2.21 | 0.43 | 1.01 | 0.13 | 0.29 |
| bone (femur + joint) | 3.74 | 1.27 | 0.70 | 0.36 | 0.08 | 0.16 |
| thyroids | −6.46 | 66.56 | 8.34 | 11.63 | 19.89 | 30.96 |
| tail | 11.75 | 0.66 | 2.57 | 1.39 | 0.28 | 0.10 |
| [$^{225}$Ac(DOTA)]$^-$ | | | | | | |
| blood | 7.2941 | 4.1461 | 0.1102 | 0.0707 | — | — |
| urine | 2691.0615 | 1906.4694 | 177.6788 | 168.4716 | — | — |
| feces | 1.5693 | 1.8307 | 0.4091 | 0.4652 | — | — |
| heart | 2.5579 | 2.0110 | 0.2857 | 0.2702 | — | — |
| liver | 2.9046 | 0.8757 | 0.2841 | 0.2157 | — | — |
| kidneys | 40.4489 | 10.8186 | 1.4787 | 0.7053 | — | — |
| lungs | 7.3872 | 1.9528 | 0.2551 | 0.1695 | — | — |
| small intestines | 3.8916 | 2.4605 | 2.0201 | 2.4443 | — | — |
| large intestines | 3.8419 | 1.8882 | 0.1381 | 0.2122 | — | — |
| brain | 0.1588 | 0.0692 | 0.0380 | 0.0968 | — | — |
| bladder | 76.0987 | 42.8592 | 6.9149 | 4.5152 | — | — |
| spleen | 1.5598 | 1.6847 | 0.2228 | 0.4642 | — | — |

TABLE 3-continued

Organ distribution of $^{225}$Ac complexes following intravenous injection in mice. Adult C57BL/6 mice were injected with [$^{225}$Ac(macropa)]$^+$, [$^{225}$Ac(DOTA)]$^-$, or $^{225}$Ac(NO$_3$)$_3$ and sacrificed after 15 min, 1 h, or 5 h. Values for each time point are given as % ID/g (n = 3) using energy window C (400-480 keV).

| Organ | 15 min | SD | 1 h | SD | 5 h | SD |
|---|---|---|---|---|---|---|
| stomach | 3.2425 | 2.1465 | 0.1720 | 0.2911 | — | — |
| pancreas | 1.0290 | 1.1339 | 0.1730 | 0.1437 | — | — |
| bone (femur + joint) | 4.4224 | 1.8431 | 0.5654 | 0.2432 | — | — |
| thyroids | −109.5394 | 150.5455 | 3.5247 | 36.1530 | — | — |
| tail | 13.4731 | 3.2236 | 1.0280 | 0.3206 | — | — |
| $^{225}$Ac(NO$_3$)$_3$ | | | | | | |
| blood | 42.3521 | 6.5376 | 11.3736 | 15.9719 | 2.1769 | 0.7500 |
| urine | 19.8282 | 14.9210 | 104.9103 | 130.5319 | 5.8548 | 8.2799 |
| feces | 0.4896 | 0.2884 | 0.1122 | 0.1587 | 0.8535 | 0.2061 |
| heart | 9.0992 | 3.1686 | 3.3464 | 4.3204 | 1.2018 | 0.1929 |
| liver | 24.1147 | 1.8809 | 23.6180 | 33.2545 | 54.1727 | 4.7696 |
| kidneys | 14.2266 | 4.1528 | 6.2070 | 7.2061 | 4.2061 | 1.5123 |
| lungs | 14.4797 | 2.7960 | 5.2078 | 7.2810 | 5.4923 | 4.6341 |
| small intestines | 2.0956 | 0.0803 | 3.5548 | 1.8035 | 1.2922 | 0.6032 |
| large intestines | 1.5716 | 0.8096 | 0.4366 | — | 1.0259 | 0.5032 |
| brain | 0.6755 | 0.2338 | 0.4402 | 0.1057 | 0.0430 | 0.0773 |
| bladder | 1.9351 | 2.1420 | 2.2929 | 1.3941 | 3.4975 | 5.8177 |
| spleen | 25.4263 | 6.0011 | 38.1082 | — | 62.2357 | 17.5694 |
| stomach | 2.4232 | 0.3667 | 2.3350 | — | 2.0358 | 1.6514 |
| pancreas | 2.4405 | 0.5887 | 1.8508 | — | 0.4643 | 0.3109 |
| bone (femur + joint) | 3.4560 | 0.9882 | 2.7213 | — | 3.5851 | 1.4683 |
| thyroids | 3.5934 | 1.5023 | 0.0000 | — | −0.4455 | 3.5100 |
| tail | 9.1381 | 7.4041 | 9.0877 | — | 28.4443 | 30.7841 |

In Vivo Studies of $^{225}$Ac-macropa-Tmab

At the time points indicated in Table 4 below, an aliquot of complex in serum was removed and either directly analyzed by radio-TLC or first mixed with excess DTPA to remove any loosely-bound $^{225}$Ac. The decay-corrected values shown represent % activity associated with the complex at R$_F$=0 on the TLC plate after exposure to an EDTA mobile phase. Reported uncertainties (±1 SD) were derived from spotting TLC plates in triplicate at each time point. The % intact complex remaining was not significantly different for samples subjected to the DTPA challenge versus those that were not (p>0.05, 2-tail t-test). The results demonstrate that $^{225}$Ac remains strongly bound by macropa-Tmab in human serum over a 7-day period.

TABLE 4

Complex stability (% intact complex remaining) of $^{225}$Ac-macropa-Tmab in human serum at 37° C.

| | 1 h | 1 day | 3 days | 7 days |
|---|---|---|---|---|
| Without DTPA Challenge | 96.4 ± 0.9 | 99.0 ± 0.5 | 98.7 ± 0.6 | 99.2 ± 0.4 |
| With DTPA Challenge | — | 91.5 ± 12 | — | 97.1 ± 1.6 |

Characterization of Eighteen-Membered Macrocyclic Ligands for Ion Chelation

Radium-223 ($^{223}$Ra) is the first therapeutic alpha (α)-emitting radionuclide to be approved for clinical use in cancer patients, and is effective in erradicating bone metastases. To harness the therapeutic potential of α-particles for soft-tissue metastases, the strategy of targeted alpha-particle therapy (TAT) has emerged, whereby lethal α-emitting radionuclides are conjugated to tumor-targeting vectors using bifunctional chelators to selectively deliver cytotoxic alpha radiation to cancer cells. Actinium-225 ($^{225}$Ac) was examined for use in TAT owing to its long 10-day half-life that is compatible with antibody-based targeting vectors and 4 high-energy α-emissions that are extremely lethal to cells. The 12-membered tetraaza macrocycle H$_4$DOTA is currently the state of the art for the chelation of the $^{225}$Ac$^{3+}$ ion, however, the thermodynamic stabilities of complexes of H$_4$DOTA decrease as the ionic radius of the metal ion increases, indicating that this ligand is not optimal for chelation of the of the Ac$^{3+}$ ion (the largest +3 ion on the periodic table). The macrocyclic complexes of the present technology provide a significant and unexpected improvement over known complexes, where the present examples (H$_2$macropa and H$_2$macropa-NCS; Scheme 1) illustrate the improved $^{225}$Ac bifunctional chelators according to the present technology.

Scheme 1. Structures of H₂macropa and H₂macropa-NCS.

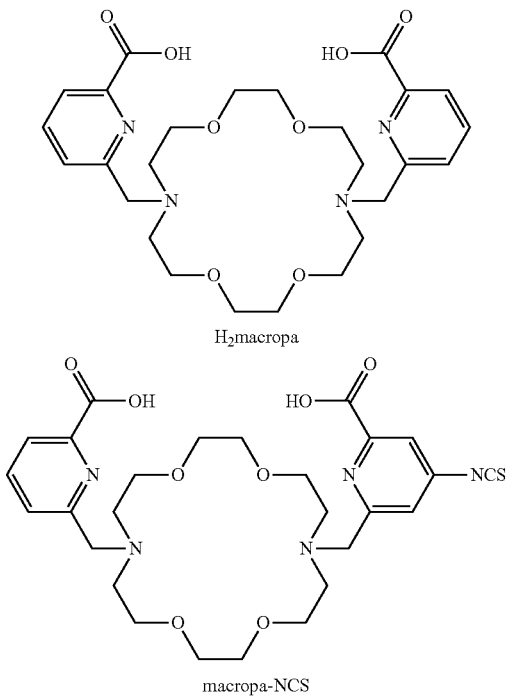

Previous studies have shown that macropa, for which the thermodynamic affinity for the whole lanthanide series was evaluated, is selective for the larger metal ions La$^{3+}$, Pb$^{2+}$, and Am$^{3+}$ over the smaller Lu$^{3+}$, Ca$^{2+}$, and Cm$^{3+}$ ions.[24-26] Without wishing to be bound by theory it was believed that macropa would effectively chelate the large Ac$^{3+}$ ion. Before assessing its Ac-chelation properties, complex formation was evaluated in situ between macropa and cold La$^{3+}$ and Lu$^{3+}$ ions. In these studies, La$^{3+}$ was used as a non-radioactive surrogate for $^{225}$Ac$^{3+}$ because it is chemically similar albeit slightly smaller (1.03 Å, CN 6). Complexation of the smaller Lu$^{3+}$ ion (0.861 Å, CN 6) by macropa was investigated to probe its size-selectivity. La$^{3+}$ and Lu$^{3+}$ titrations confirmed the high affinity of these metal ions for macropa at pH 7.4, consistent with the previously measured stability constants (log $K_{LaL}$=14.99, log $K_{LuL}$=8.25).[24] The kinetic inertness of these complexes formed in situ was investigated by challenging them with an excess of either ethylenediaminetetraacetic acid (EDTA) or diethylenetriaminepentaacetic acid (DTPA) chelators that have a higher thermodynamic affinity than macropa for Lu$^{3+}$ and La$^{3+}$ ions.[27] The Lu$^{3+}$ ion was transchelated within 1 min upon the addition of only 10 equiv of EDTA, whereas the La$^{3+}$ complex remained intact for up to 21 days in the presence of 1000 equiv of DTPA. These results demonstrate that, despite a strong thermodynamic preference for DTPA to transchelate La$^{3+}$, the high level of kinetic inertness of the macropa complex inhibits this process on a detectable time scale.

The La$^{3+}$ and Lu$^{3+}$ complexes of macropa were isolated and their solid-state structures were elucidated by X-ray crystallography (FIGS. 1A-1D). The La$^{3+}$ and Lu$^{3+}$ ions reside above the 18-membered macrocycle, and the two picolinate arms are positioned on the same side of the macrocycle. The coordination sphere of the Lu$^{3+}$ ion is satisfied by the ten donors of macropa with both picolinate arms deprotonated; by contrast, the larger La$^{3+}$ ion forms an 11-coordinate complex by the incorporation of an inner-sphere water molecule that penetrates the macrocycle. The ability of macropa to form stable 11-coordinate complexes is of particular significance because recent EXAFS studies have demonstrated that Ac$^{3+}$ prefers a coordination number of 11 in aqueous solutions.[29,30]

Macropa was examined for the chelation of the larger, radioactive $^{225}$Ac$^{3+}$ ion and compared to DOTA. Both ligands (59 µM) were incubated with $^{225}$Ac (26 kBq) in 0.15 M NH₄OAc buffer at pH 5.5-6, and the complexation reaction was monitored by radio-TLC after 5 min. Remarkably, macropa complexed all the $^{225}$Ac after merely 5 min at RT, whereas DOTA only complexed 10% under these conditions. At 100-fold lower concentration (0.59 µM) of macropa, a L:M ratio of only 1800, radiolabeling was still complete at RT in 5 min. At this concentration, DOTA failed to form a complex with $^{225}$Ac. Taken together, these studies reveal macropa to exhibit excellent radiolabeling kinetics at ambient temperature and submicromolar ligand concentration, conditions under which DOTA fails.

The long half-life of $^{225}$Ac necessitates its stable complex retention in vivo to avoid off-target damage to normal tissues arising from the release of free $^{225}$Ac$^{3+}$. Furthermore, the stability of $^{225}$Ac complexes against transmetalation and transchelation needs to be high. To determine the kinetic inertness, [$^{225}$Ac(macropa)]$^+$ was challenged with La$^{3+}$ because of the established high affinity of macropa for this metal ion. A 50-fold excess of La$^{3+}$ with respect to ligand concentration was added to $^{225}$Ac-radiolabeled solutions of macropa (0.59 µM) at RT. Over 7 days, 98% of the $^{225}$Ac complex remained intact by radio-TLC, signifying that a large molar equivalent of La$^{3+}$ is unable to displace $^{225}$Ac$^{3+}$. The stability of [$^{225}$Ac(macropa)]$^+$ in human serum was also evaluated by radio-TLC and revealed that $^{225}$Ac$^{3+}$ remains complexed by macropa for at least 8 days.

Evaluation of the Biodistribution of [$^{225}$Ac(macropa)]$^+$ Complexes

Figure 2A:
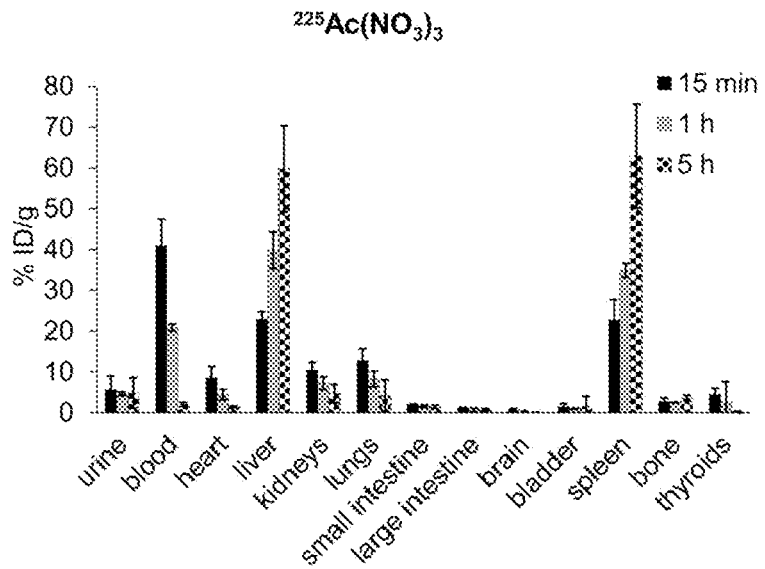
Figure 2B:
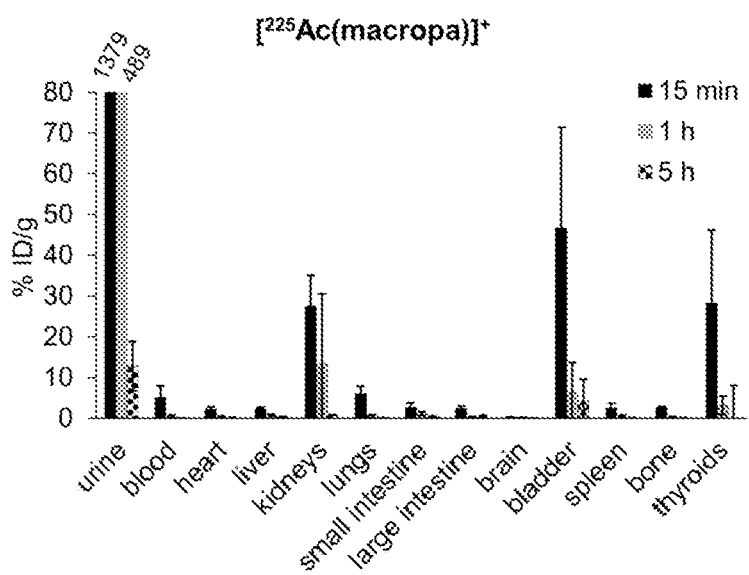
FIG. 2B, top view).
Figure 2C:
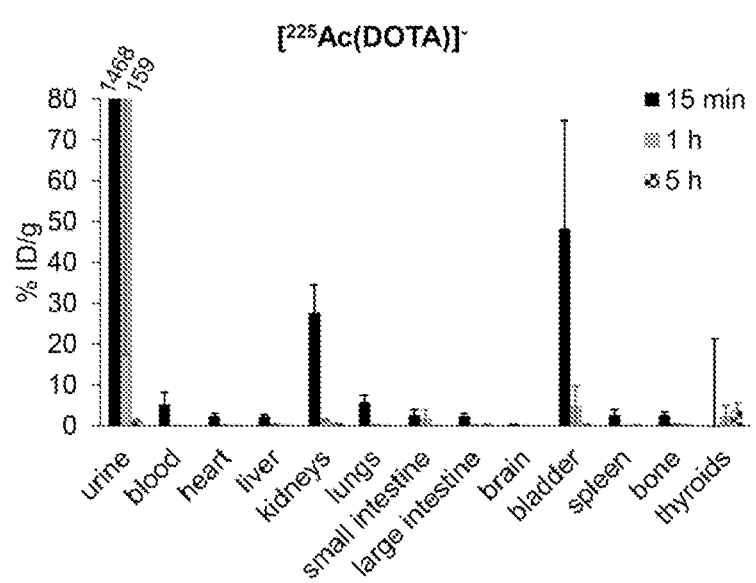

The in vivo stability [$^{225}$Ac(macropa)]$^+$ was examined by comparing its biodistribution to those of $^{225}$Ac(NO₃)₃ and [$^{225}$Ac(DOTA)]$^-$. C57BL/6 mice were injected via tail vein with 10-50 kBq of each radiometal complex and were sacrificed after 15 min, 1 h, or 5 h. The amount of $^{225}$Ac retained in each organ was quantified by gamma counting and reported as the percent of injected dose per gram of tissue (% ID/g). The results of these studies are compiled in Tables 1-3. Inadequate stability of an $^{225}$Ac complex leading to the loss of radioisotope in vivo is manifested by the accumulation of $^{225}$Ac in the liver, spleen, and bone of mice.[11,12,32] FIG. 2A demonstrates slow blood clearance and excretion, coupled to large accumulation in the liver and spleen of the uncomplexed $^{225}$Ac(NO₃)₃. The biodistribution profile of [$^{225}$Ac(macropa)]$^+$ (FIG. 3B) differs markedly from that of $^{225}$Ac(NO₃)₃. [$^{225}$Ac(macropa)]$^+$ was rapidly cleared from mice, with very little activity measured in blood by 1 h post injection. Most of the injected dose was renally excreted and subsequently detected in the urine, demonstrating the moderate kidney and bladder uptake of [$^{225}$Ac(macropa)]$^+$ observed in mice at 15 min and 1 h post injection. Of significance, [$^{225}$Ac(macropa)]$^+$ did not accumulate in any organ over the time course of the study, indicating that the complex does not release free $^{225}$Ac$^{3+}$ in vivo. Its biodistribution profile was similar to that of [$^{225}$Ac(DOTA)]$^-$ (FIG. 3C), which has been previously shown to retain $^{225}$Ac$^{3+}$ in vivo.[7]

Synthesis and Characterization of [$^{225}$Ac(macropa)]$^+$ TAT Complexes

Due to the inherent stability of the [$^{225}$Ac(macropa)]$^+$ complexes, macropa was incorporated into into tumor-targeting constructs. To facilitate its conjugation, a reactive isothiocyanate functional group was installed onto one of the picolinate arms of macropa to give the novel bifunctional ligand macropa-NCS (Scheme 1). As illustrated in vide supra, macropa-NCS was synthesized over 8 steps and characterized by conventional techniques. For one tumor-targeting construct, macropa-NCS was s conjugated to trastuzumab (Tmab), an FDA-approved monoclonal antibody that targets the human epidermal growth factor receptor 2 (HER2) in breast and other cancers.[33] With a biological half-life of several weeks,[34,35] Tmab is an ideal vector to shuttle the long-lived $^{225}$Ac radionuclide to tumor cells. $^{225}$Ac-macropa-Tmab displayed excellent stability in human serum at 37° C.; after 7 days, >99% of the complex remained intact (Table 4). Together, these results highlight the efficacy of macropa as a chelator for $^{225}$Ac in antibody constructs as well as other cancer-targeted constructs.

REFERENCES

7. M. R. McDevitt, D. Ma, L. T. Lai, J. Simon, P. Borchardt, R. K. Frank, K. Wu, V. Pellegrini, M. J. Curcio, M. Miederer, et al., *Science* 2001, 294, 1537.
11. I. A. Davis, K. A. Glowienka, R. A. Boll, K. A. Deal, M. W. Brechbiel, M. Stabin, P. N. Bochsler, S. Mirzadeh, S. J. Kennel, *Nucl. Med. Biol.* 1999, 26, 581.
12. K. A. Deal, I. A. Davis, S. Mirzadeh, S. J. Kennel, M. W. Brechbiel, *J. Med. Chem.* 1999, 42, 2988.
24. A. Roca-Sabio, M. Mato-Iglesias, D. Esteban-Gómez, É. Tóth, A. de Blas, C. Platas-Iglesias, T. Rodríguez-Blas, *J. Am. Chem. Soc.* 2009, 131, 3331.
25. R. Ferreirós-Martínez, D. Esteban-Gómez, É. Tóth, A. de Blas, C. Platas-Iglesias, T. Rodríguez-Blas, *Inorg. Chem.* 2011, 50, 3772.
26. M. P. Jensen, R. Chiarizia, I. A. Shkrob, J. S. Ulicki, B. D. Spindler, D. J. Murphy, M. Hossain, A. Roca-Sabio, C. Platas-Iglesias, A. de Blas, et al., *Inorg. Chem.* 2014, 53, 6003.
27. A. E. Martell, R. M. Smith, *Critical Stability Constants: Vol. 1*, Plenum Press, New York; London, 1974.
29. M. G. Ferrier, E. R. Batista, J. M. Berg, E. R. Birnbaum, J. N. Cross, J. W. Engle, H. S. La Pierre, S. A. Kozimor, J. S. Lezama Pacheco, B. W. Stein, et al., *Nat. Commun.* 2016, 7, 12312.
30. M. G. Ferrier, B. W. Stein, E. R. Batista, J. M. Berg, E. R. Birnbaum, J. W. Engle, K. D. John, S. A. Kozimor, J. S. Lezama Pacheco, L. N. Redman, *ACS Cent. Sci.* 2017, 3, 176.
32. G. J. Beyer, R. Bergmann, K. Schomäcker, F. Rösch, G. Schäfer, E. V Kulikov, A. F. Novgorodov, *Isot. Isot. Environ. Heal. Stud.* 1990, 26, 111.
33. M. M. Moasser, *Oncogene* 2007, 26, 6469.
34. B. Leyland-Jones, K. Gelmon, J.-P. Ayoub, A. Arnold, S. Verma, R. Dias, P. Ghahramani, *J. Clin. Oncol.* 2003, 21, 3965.
35. D. Leveque, L. Gigou, J. P. Bergerat, *Curr. Clin. Pharmacol.* 2008, 3, 51.
37. A. P. Kozikowski, F. Nan, P. Conti, J. Zhang, E. Ramadan, T. Bzdega, B. Wroblewska, J. H. Neale, S. Pshenichkin, J. T. Wroblewski, *J. Med. Chem.* 2001, 44, 298.
38. K. P. Maresca, S. M. Hillier, F. J. Femia, D. Keith, C. Barone, J. L. Joyal, C. N. Zimmerman, A. P. Kozikowski, J. A. Barrett, W. C. Eckelman, et al., *J. Med. Chem.* 2009, 52, 347.
39. S. M. Hillier, K. P. Maresca, F. J. Femia, J. C. Marquis, C. A. Foss, N. Nguyen, C. N. Zimmerman, J. A. Barrett, W. C. Eckelman, M. G. Pomper, et al., *Cancer Res.* 2009, 69, 6932.
40. J. A. Barrett, R. E. Coleman, S. J. Goldsmith, S. Vallabhajosula, N. A. Petry, S. Cho, T. Armor, J. B. Stubbs, K. P. Maresca, M. G. Stabin, et al., *J. Nucl. Med.* 2013, 54, 380.
41. J. Kelly, A. Amor-Coarasa, A. Nikolopoulou, D. Kim, C. Williams Jr., S. Ponnala, J. W. Babich, *Eur. J. Nucl. Med. Mol. Imaging* 2017, 44, 647.
42. A. Ghosh, W. D. W. Heston, *J. Cell. Biochem.* 2004, 91, 528.
43. M. S. Dennis, M. Zhang, Y. Gloria Meng, M. Kadkhodayan, D. Kirchhofer, D. Combs, L. A. Damico, *J. Biol. Chem.* 2002, 277, 35035.
44. C. E. Dumelin, S. Trüssel, F. Buller, E. Trachsel, F. Bootz, Y. Zhang, L. Mannocci, S. C. Beck, M. Drumea-Mirancea, M. W. Seeliger, et al., *Angew. Chem. Int. Ed.* 2008, 47, 3196.
102. M. Mato-Iglesias, A. Roca-Sabio, Z. Pálinkás, D. Esteban-Gómez, C. Platas-Iglesias, É. Tóth, A. de Blas, T. Rodríguez-Blas, *Inorg. Chem.* 2008, 47, 7840-7851.
103. A. Roca-Sabio, M. Mato-Iglesias, D. Esteban-Gómez, É. Tóth, A. de Blas, C. Platas-Iglesias, T. Rodríguez-Blas, *J. Am. Chem. Soc.* 2009, 131, 3331-3341.
104. V. J. Gatto, G. W. Gokel, *J. Am. Chem. Soc.* 1984, 106, 8240-8244.
105. E. R. Neil, M. A. Fox, R. Pal, L.-O. Palsson, B. A. O'Sullivan, D. Parker, *Dalton Trans.* 2015, 44, 14937-14951.
106. Z. E. A. Chamas, X. Guo, J.-L. Canet, A. Gautier, D. Boyer, R. Mahiou, *Dalton Trans.* 2010, 39, 7091-7097.
108. D. T. Corson, C. F. Meares, *Bioconjug. Chem.* 2000, 11, 292-299.
109. G. M. Sheldrick, *Acta Crystallogr. Sect. A* 2015, 71, 3-8.
110. G. M. Sheldrick, *Acta Crystallogr. Sect. A* 2008, 64, 112-122.
111. P. Müller, *Crystallogr. Rev.* 2009, 15, 57-83.
112. O. V Dolomanov, L. J. Bourhis, R. J. Gildea, J. A. K. Howard, H. Puschmann, *J. Appl. Crystallogr.* 2009, 42, 339-341.
113. J. Dilling, R. Krücken, L. Merminga, Eds., *ISAC and ARIEL: The TRIUMF Radioactive Beam Facilities and the Scientific Program*, Springer, Dordrecht, Netherlands, 2014.
114. J. R. Crawford, P. Kunz, H. Yang, P. Schaffer, T. J. Ruth, *Appl. Radiat. Isot.* 2017, 122, 222-228.
115. B. Zielinska, C. Apostolidis, F. Bruchertseifer, A. Morgenstern, *Solvent Extr. Ion Exch.* 2007, 25, 339-349.
116. V. Radchenko, J. W. Engle, J. J. Wilson, J. R. Maassen, F. M. Nortier, W. A. Taylor, E. R. Birnbaum, L. A. Hudston, K. D. John, M. E. Fassbender, *J. Chromatogr. A* 2015, 1380, 55-63.
117. M. P. Miranda-Hernández, E. R. Valle-González, D. Ferreira-Gómez, N. O. Pérez, L. F. Flores-Ortiz, E. Medina-Rivero, *Anal. Bioanal. Chem.* 2016, 408, 1523-1530.
118. E. W. Price, K. J. Edwards, K. E. Carnazza, S. D. Carlin, B. M. Zeglis, M. J. Adam, C. Orvig, J. S. Lewis, *Nucl. Med. Biol.* 2016, 43, 566-576.

119. J. Kelly, A. Amor-Coarasa, A. Nikolopoulou, D. Kim, C. Williams, S. Ponnala, J. W. Babich, *Eur. J. Nucl. Med. Mol. Imaging* 2017, 44, 647-661.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A composition of Formula I

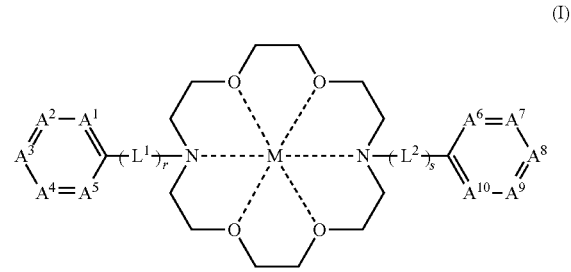

or a pharmaceutically acceptable salt thereof, wherein
M is an alpha-emitting radionuclide;
$A^1$ is N or $CR^1$;
$A^2$ is N or $CR^2$;
$A^3$ is N or $CR^3$;
$A^4$ is N or $CR^4$;
$A^5$ is N or $CR^5$;
$A^6$ is N or $CR^6$;
$A^7$ is N or $CR^7$;
$A^8$ is N or $CR^8$;
$A^9$ is N or $CR^9$;
$A^{10}$ is N or $CR^{10}$; provided that no more than three of $A^1$, $A^2$, $A^3$, $A^4$, and $A^5$ are N, and no more than three of $A^6$, $A^7$, $A^8$, $A^9$, and $A^{10}$ are N;
$R^1$, $R^2$, $R^3$, $R^4$, $R^5$, $R^6$, $R^7$, $R^8$, $R^9$, and $R^{10}$ are each independently selected from H, alkyl, cycloalkyl, alkenyl, cycloalkenyl, alkynyl, aryl, heterocyclyl, heteroaryl, halo, —OR', —$(OCH_2CH_2)_x$—R' (where x is 1, 2, 3, 4, 5, 6, 7, 8, 9, or 10), —$(OCH_2CH_2)_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —$SO_2$R', —$SO_2$(OR'), —$SO_2$NR'$_2$, —P(O)(OR')$_2$, —P(O)R'

(OR'), —P(O)R'$_2$, —NO$_2$, —CN, —OCN, —SCN, —NCO, —NCS, —NR'—NR'R', —N$_3$, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N$_3$, —N=C=N—R', —SO$_2$Cl, —C(O)Cl, and the epoxide group are each independently linked to the carbon atom to which it is attached by a —(CH$_2$)$_x$-linker where n is 1, 2, or 3;

or one or two pairs of directly adjacent $R^1$, $R^2$, $R^3$, $R^4$, $R^5$, $R^6$, $R^7$, $R^8$, $R^9$, and $R^{10}$ groups are interconnected to form a five- to six-membered substituted or unsubstituted carbocyclic or nitrogen-containing ring;

R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl, or wherein two R' groups attached to the same atom are interconnected to form a three- to six-membered ring, $L^1$ and $L^2$ are each independently selected from —(CH$_2$)$_p$—, where p is a value of 1, 2, or 3;

r is 0 or 1; and s is 0 or 1.

B. The composition of Paragraph A, wherein at least one of $A^1$, $A^2$, $A^3$, $A^4$, $A^5$, $A^6$, $A^7$, $A^8$, $A^9$, and $A^{10}$ is N.

C. The composition of Paragraph A or Paragraph B, wherein at least one of $A^1$, $A^2$, $A^3$, $A^4$, and $A^5$ is N and at least one of $A^6$, $A^7$, $A^8$, $A^9$, and $A^{10}$ is N.

D. The composition of Paragraph A or Paragraph B, wherein $A^1$, $A^2$, $A^3$, $A^4$, and $A^5$ are not N.

E. The composition of Paragraph A or Paragraph B, wherein $A^6$, $A^7$, $A^8$, $A^9$, and $A^{10}$ are not N.

F. The composition of any one of Paragraphs A and D-E, wherein the composition of Formula I is a composition of Formula I-a

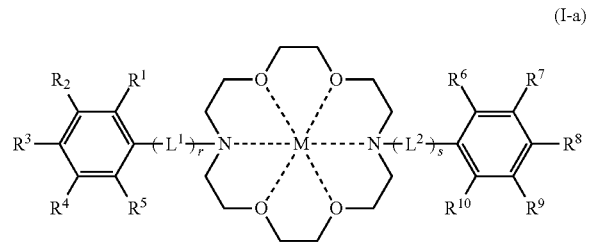

(I-a)

or a pharmaceutically acceptable salt thereof.

G. The composition of any one of Paragraphs A-F, wherein at least one of $R^1$, $R^2$, $R^3$, $R^4$, $R^5$, $R^6$, $R^7$, $R^8$, $R^9$, and $R^{10}$ is a group selected from —C(O)R', —C(S)R', —OCN, —SCN, —NCO, —NCS, —NR'—NR'R', —N$_3$, —N=C=N—R', —SO$_2$Cl, —C(O)Cl, and an epoxide group.

H. The composition of any one of Paragraphs A-F, wherein at least one of $R^1$, $R^2$, $R^3$, $R^4$, $R^5$, $R^6$, $R^7$, $R^8$, $R^9$, and $R^{10}$ is a group selected from halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, and —CN.

I. The composition of any one of Paragraphs A-H, wherein at least one of r and s is 1.

J. The composition of any one of Paragraphs A-J, wherein at least one of r and s is 0.

K. The composition of Paragraphs A-C and G-J, wherein the composition of Formula I is a composition of Formula I-b

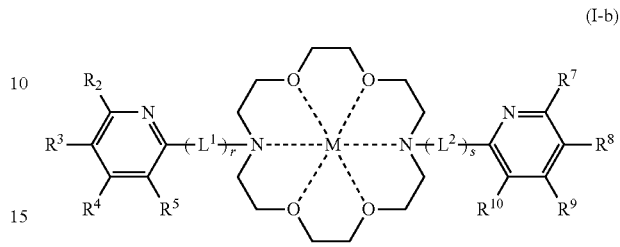

(I-b)

or a pharmaceutically acceptable salt thereof.

L. The composition of any one of Paragraphs A-K, wherein one or two pairs of directly adjacent groups among $R^1$, $R^2$, $R^3$, $R^4$, $R^5$, $R^6$, $R^7$, $R^8$, $R^9$, and $R^{10}$ groups are interconnected to form a substituted or unsubstituted four- to six-membered carbocyclic or nitrogen-containing ring.

M. The composition of any one of Paragraphs A-C, G-J, and L, wherein the composition of Formula I is a composition of Formula I-v

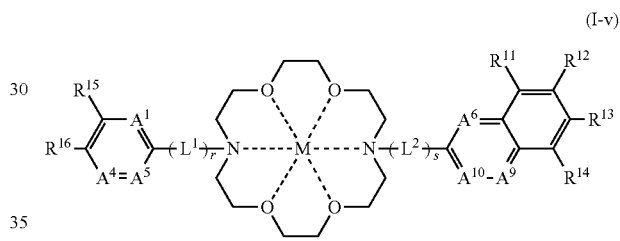

(I-v)

or a pharmaceutically acceptable salt thereof, wherein $R^{11}$, $R^{12}$, $R^{13}$, $R^{14}$, $R^{15}$, and $R^{16}$ are each independently selected from the group consisting of H, alkyl, cycloalkyl, alkenyl, cycloalkenyl, alkynyl, aryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N$_3$, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N$_3$, —N=C=N—R', —SO$_2$Cl, —C(O)Cl, and the epoxide group are each independently linked to the carbon atom to which it is attached by a —(CH$_2$)$_x$-linker where n is 1, 2, or 3; and wherein R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl.

N. The composition of any one of Paragraphs A-C, G-J, and L, wherein the composition of Formula I is a composition of Formula I-w

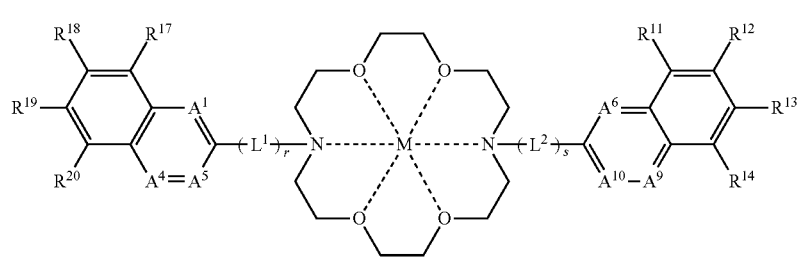

(I-w)

or a pharmaceutically acceptable salt thereof, wherein $R^{11}$, $R^{12}$, $R^{13}$, $R^{14}$, $R^{17}$, $R^{18}$, $R^{19}$, and $R^{20}$ are each independently selected from the group consisting of H, alkyl, cycloalkyl, alkenyl, cycloalkenyl, alkynyl, aryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR' R', —NR' C(O)NR', —NR' C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3; and wherein R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl.

O. The composition of any one of Paragraphs A-C, G-J, L, and N, wherein the composition is of Formula I-x

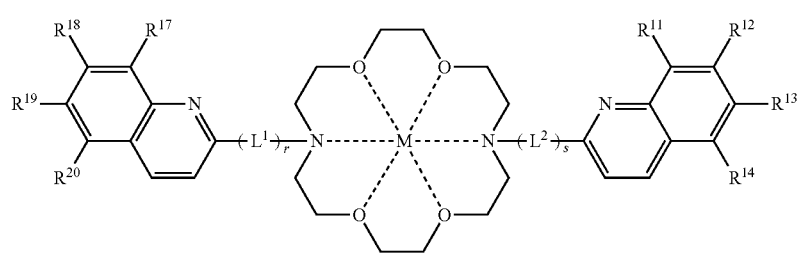

(I-x)

or a pharmaceutically acceptable salt thereof.

P. The composition of any one of Paragraphs A-O, wherein M is selected from actinium-225 ($^{225}$Ac$^{3+}$), radium-223 ($^{233}$Ra$^{2+}$), bismuth-213 ($^{213}$Bi$^{3+}$), lead-212 ($^{212}$Pb$^{2+}$ and/or $^{212}$Pb$^{4+}$), terbium-149 ($^{149}$Tb$^{3+}$), fermium-255 ($^{255}$Fm$^{3+}$), thorium-227 ($^{227}$Th$^{4+}$), thorium-226 ($^{226}$Th$^{4+}$), astatine-211 ($^{211}$At$^+$), astatine-217 ($^{217}$At$^+$), and uranium-230.

Q. A composition useful in targeted radiotherapy of cancer, wherein the composition is of Formula II

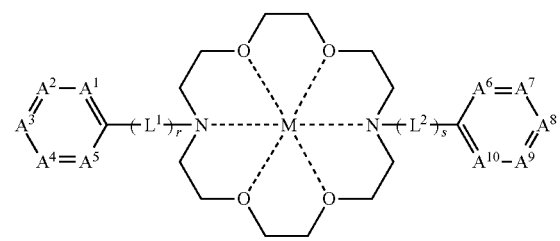

(II)

or a pharmaceutically acceptable salt thereof, wherein
M is an alpha-emitting radionuclide;
$A^1$ is N or $CR^1$;
$A^2$ is N or $CR^2$;
$A^3$ is N or $CR^3$;
$A^4$ is N or $CR^4$;
$A^5$ is N or $CR^5$;
$A^6$ is N or $CR^6$;
$A^7$ is N or $CR^7$;
$A^8$ is N or $CR^8$;
$A^9$ is N or $CR^9$;
$A^{10}$ is N or $CR^{10}$; provided that no more than three of $A^1$, $A^2$, $A^3$, $A^4$, and $A^5$ are N, and no more than three of $A^6$, $A^7$, $A^8$, $A^9$, and $A^{10}$ are N;
at least one of $R^1$, $R^2$, $R^3$, $R^4$, $R^5$, $R^6$, $R^7$, $R^8$, $R^9$ and $R^{10}$ is a selective cancer cell targeting group or a selective cancer cell targeting group linked to the carbon atom to which it is attached by a alkylene, —O—, —(OCH$_2$CH$_2$)$_z$— (where z is 1, 2, 3, 4, 5, 6, 7, 8, 9, or 10), —S—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')—, optionally wherein —O—, —(OCH$_2$CH$_2$)$_x$—, —S—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')— are each independently linked to the carbon atom to which it is attached by a C$_1$-C$_3$ alkylene;

the remaining R$^1$, R$^2$, R$^3$, R$^4$, R$^5$, R$^6$, R$^7$, R$^8$, R$^9$, and R$^{10}$ are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is independently at each occurrence 1, 2, or 3;

or one or two pairs of directly adjacent R$^1$, R$^2$, R$^3$, R$^4$, R$^5$, R$^6$, R$^7$, R$^8$, R$^9$, and R$^{10}$ groups are interconnected to form a five- to six-membered substituted or unsubstituted carbocyclic or nitrogen-containing ring;

R' is independently at each occurrence H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl, or wherein two R' groups attached to the same atom are interconnected to form a three- to six-membered ring, L$^1$ and L$^2$ are each independently selected from —(CH$_2$)$_p$—, where p is a value of 1, 2, or 3;

r is 0 or 1; and s is 0 or 1.

R. The composition of Paragraph Q, wherein said selective cancer cell targeting group contains amino acids linked by peptide bonds.

S. The composition of Paragraph Q or Paragraph R, wherein said selective cancer cell targeting group is a cancer-targeting antibody or antibody fragment.

T. The composition of Paragraph Q or Paragraph R, wherein said selective cancer cell targeting group is an oligopeptide containing up to 50 amino acids.

U. A method of treating cancer in a subject, the method comprising administering to a subject having cancer an effective amount of a composition of Formula II

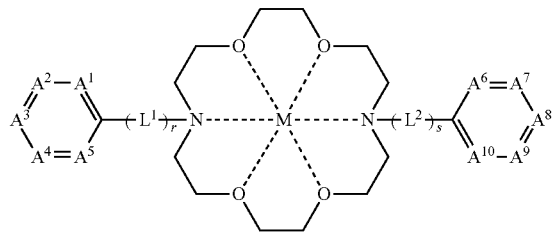

(II)

or a pharmaceutically acceptable salt thereof, wherein:
M is an alpha-emitting radionuclide;
A$^1$ is N or CR$^1$;
A$^2$ is N or CR$^2$;
A$^3$ is N or CR$^3$;
A$^4$ is N or CR$^4$;
A$^5$ is N or CR$^5$;
A$^6$ is N or CR$^6$;
A$^7$ is N or CR$^7$;
A$^8$ is N or CR$^8$;
A$^9$ is N or CR$^9$;
A$^{10}$ is N or CR$^{10}$; provided that no more than three of A$^1$, A$^2$, A$^3$, A$^4$, and A$^5$ are N, and no more than three of A$^6$, A$^7$, A$^8$, A$^9$, and A$^{10}$ are N;

at least one of R$^1$, R$^2$, R$^3$, R$^4$, R$^5$, R$^6$, R$^7$, R$^8$, R$^9$, and R$^{10}$ is a selective cancer cell targeting group or a selective cancer cell targeting group linked to the carbon atom to which it is attached by a alkylene, —O—, —(OCH$_2$CH$_2$)$_z$—, —S—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')—, optionally wherein —O—, —(OCH$_2$CH$_2$)$_z$—, —S—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')— are each independently linked to the carbon atom to which it is attached by a C$_1$-C$_3$ alkylene;

the remaining R$^1$, R$^2$, R$^3$, R$^4$, R$^5$, R$^6$, R$^7$, R$^8$, R$^9$, and R$^{10}$ are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —$(CH_2)_n$— linker where n is 1, 2, or 3;

or one or two pairs of directly adjacent $R^1$, $R^2$, $R^3$, $R^4$, $R^5$, $R^6$, $R^7$, $R^8$, $R^9$, and $R^{10}$ groups are interconnected to form a five- to six-membered substituted or unsubstituted carbocyclic or nitrogen-containing ring;

R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl, or wherein two R' groups attached to the same atom are interconnected to form a three- to six-membered ring, $L^1$ and $L^2$ are each independently selected from —$(CH_2)_p$—, where p is a value of 1, 2, or 3;

r is 0 or 1; and s is 0 or 1.

V. The method of Paragraph U, wherein said selective cancer cell targeting group contains amino acids linked by peptide bonds.

W. The method of Paragraph U or Paragraph V, wherein said selective cancer cell targeting group is a cancer-targeting antibody or antibody fragment.

X. The method of Paragraph U or Paragraph V, wherein said selective cancer cell targeting group is an oligopeptide containing up to 50 amino acids.

Y. The composition of any one of Paragraphs Q-T, or a method of any one of Paragraphs U-X, wherein M is selected from actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^+$), astatine-217 ($^{217}At^+$), and uranium-230.

Z. A composition comprising a pharmaceutically acceptable carrier and a composition of any one of Paragraphs A-T. Other embodiments are set forth in the following claims, along with the full scope of equivalents to which such claims are entitled.

What is claimed is:

1. A composition of Formula I

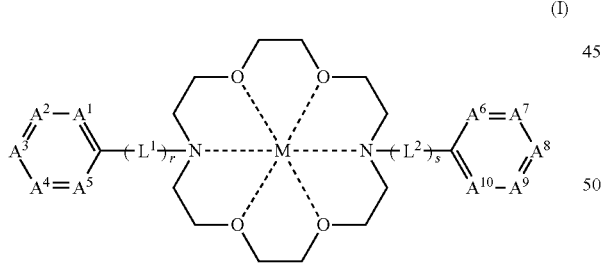

(I)

or a pharmaceutically acceptable salt thereof, wherein
M is an alpha-emitting radionuclide;
$A^1$ is N or $CR^1$;
$A^2$ is N or $CR^2$;
$A^3$ is N or $CR^3$;
$A^4$ is N or $CR^4$;
$A^5$ is N or $CR^5$;
$A^6$ is N or $CR^6$;
$A^7$ is N or $CR^7$;
$A^8$ is N or $CR^8$;
$A^9$ is N or $CR^9$;
$A^{10}$ is N or $CR^{10}$; provided that no more than three of $A^1$, $A^2$, $A^3$, $A^4$, and $A^5$ are N, no more than three of $A^6$, $A^7$, $A^8$, $A^9$, and $A^{10}$ are N, and at least one of $A^1$, $A^2$, $A^3$, $A^4$, $A^5$, $A^6$, $A^7$, $A^8$, $A^9$, and $A^{10}$ is N;

$R^1$, $R^2$, $R^3$, $R^4$, $R^5$, $R^6$, $R^7$, $R^8$, $R^9$, and $R^{10}$ are each independently selected from H, alkyl, cycloalkyl, alkenyl, cycloalkenyl, alkynyl, aryl, heterocyclyl, heteroaryl, halo, —OR', —$(OCH_2CH_2)_x$—R' where x is 1, 2, 3, 4, 5, 6, 7, 8, 9, or 10, —$(OCH_2CH_2)_y$—OR' where y is 1, 2, 3, 4, 5, 6, 7, 8, 9, or 10, —SR', —OC(O)R', —C(O)OR', —C(S)OR', —C(O)NR'R', —C(S)NR'R', —NR' C(O)R', —NR'C(S)R', —NR'R', —NR'C(o)NR', —NR' C(S)NR', —S(O)R', —$SO_2R'$, —$SO_2(OR')$, —$SO_2NR'_2$, —P(O)(OR')$_2$, —P(O)R'(OR'), —P(O)R'$_2$, —$NO_2$, —CN, —OCN, —SCN, —NCO, —NCS, —NR'—NR'R', —N, —N=C=N—R', —$SO_2Cl$, —C(O)Cl, and an epoxide group, optionally wherein halo, —OR', —$(OCH_2CH_2)_x$—R', —$(OCH_2CH_2)_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —$SO_2R'$, —$SO_2(OR')$, —$SO_2NR'_2$, —P(O)(OR')$_2$, —P(O)R'(OR'), —P(O)R'$_2$, —$NO_2$, —CN, —OCN, —SCN, —NCO, —NCS, —NR'—NR'R', —N, —N=C=N—R', —$SO_2Cl$, —C(O)Cl, and the epoxide group are each independently linked to the carbon atom to which it is attached by a —$(CH_2)_n$— linker where n is 1, 2, or 3;

wherein at least one of R', $R^2$, $R^3$, $R^4$, $R^5$, $R^6$, $R^7$, $R^8$, $R^9$, and $R^{10}$ is a group selected from —C(O)R', —C(S)R', —OCN, —SCN, —NCO, —NCS, —NR'—NR'R', —$N_3$, —N=C=N—R', —$SO_2Cl$, —C(O)Cl, and an epoxide group;

R' is independently at each occurrence H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl, or wherein two R' groups attached to the same atom are interconnected to form a three- to six-membered ring, $L^1$ and $L^2$ are each independently selected from —$(CH_2)_p$—, where p is a value of 1, 2, or 3;

r is 0 or 1; and s is 0 or 1.

2. The composition of claim 1, wherein at least one of $A^1$, $A^2$, $A^3$, $A^4$, and $A^5$ is N and at least one of $A^6$, $A^7$, $A^8$, $A^9$, and $A^{10}$ is N.

3. The composition of claim 1, wherein the composition of Formula I is a composition of Formula I-b

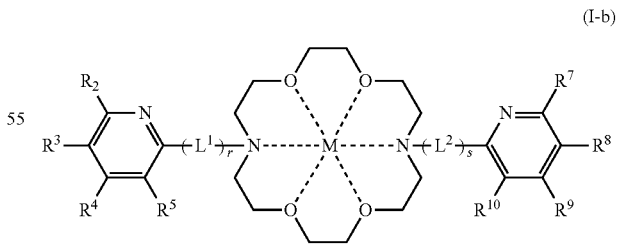

(I-b)

or a pharmaceutically acceptable salt thereof.

4. The composition of claim 1, wherein one or two pairs of directly adjacent groups among $R^1$, $R^2$, $R^3$, $R^4$, $R^5$, $R^6$, $R^7$, le, $R^9$, and $R^{10}$ groups are interconnected to form a substituted or unsubstituted four- to six-membered carbocyclic or nitrogen-containing ring.

5. The composition of claim 4, wherein the composition of Formula I is a composition of Formula I-v

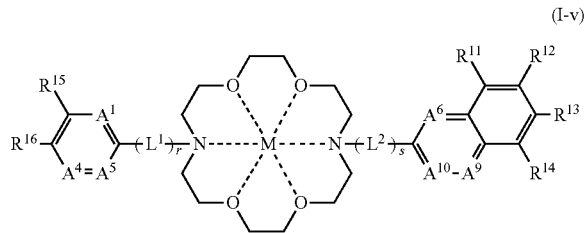

(I-v)

or a pharmaceutically acceptable salt thereof, wherein
$R^{11}$, $R^{12}$, $R^{13}$, $R^{14}$, $R^{15}$, and $R^{16}$ are each independently selected from the group consisting of H, alkyl, cycloalkyl, alkenyl, cycloalkenyl, alkynyl, aryl, halo, —OR', —(OCH$_2$CH$_2$)$_x$—R' where x is 1, 2, 3, 4, 5, 6, 7, 8, 9, or 10, —(OCH$_2$CH$_2$)$_y$—OR' where y is 1, 2, 3, 4, 5, 6, 7, 8, 9, or 10, —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N$_3$, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR,'—SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3; and
wherein R' is independently at each occurence H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl.

6. The composition of claim 5, wherein at least one of $R^{11}$, $R^{12}$, $R^{13}$, $R^{14}$, $R^{15}$, and $R^{16}$ is a group selected from —C(O)R', —C(S)R', —OCN, —SCN, —NCO, —NCS, —NR'—NR'R', —N$_3$, —N=C=N—R', —SO$_2$Cl, —C(O)Cl, and an epoxide group.

7. The composition of claim 5, wherein at least one of $R^{11}$, $R^{12}$, $R^{13}$, $R^{14}$, $R^{15}$, and $R^{16}$ is a group selected from halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, and —CN.

8. The composition of claim 4, wherein the composition of Formula I is a composition of Formula I-w

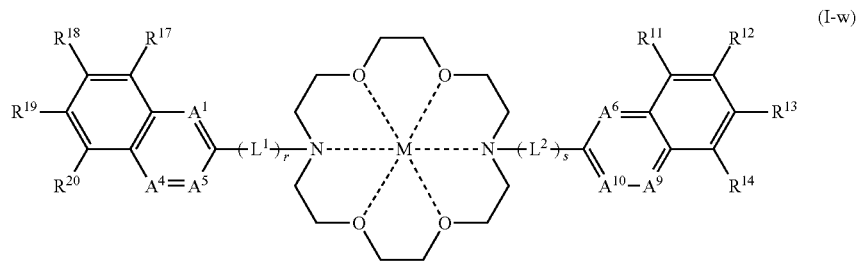

(I-w)

or a pharmaceutically acceptable salt thereof, wherein
$R^{11}$, $R^{12}$, $R^{13}$, $R^{14}$, $R^{17}$, $R^{18}$, $R^{19}$ and $R^{20}$ are each are each independently selected from the group consisting of H, alkyl, cycloalkyl, alkenyl, cycloalkenyl, alkynyl, aryl, halo, —OR', —(OCH$_2$CH$_2$)$_x$—R' where x is 1, 2, 3, 4, 5, 6, 7, 8, 9, or 10, —(OCH$_2$CH$_2$)$_y$—OR' where y is 1, 2, 3, 4, 5, 6, 7, 8, 9, or 10, —SR', —OC(O)R', —C(O)OR', —C(S)OR', —C(O)NR'R', —C(S)NR'R', —NR'C(O)R', —NR'C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR' C(O)R', —NR' C(S)R', —NR'R', —NR'C(O)NR', —NR'C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3; and
wherein R' is independently at each occurence H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl.

9. The composition of claim 8, wherein the composition of Formula I-w is a composition of Formula I-x (I-x)

[Chemical structure diagram showing a bis-quinoline complex with metal M coordinated through two nitrogen atoms and four oxygen atoms in a cage-like structure, with substituents R$^{17}$, R$^{18}$, R$^{19}$, R$^{20}$ on the left quinoline and R$^{11}$, R$^{12}$, R$^{13}$, R$^{14}$ on the right quinoline, connected via L$^1$ and L$^2$ linkers]

or a pharmaceutically acceptable salt thereof.

10. The composition of claim 1, wherein M is selected from actinium-225, radium-223, bismuth-213, lead-212, terbium-149, fermium-255, thorium-227, thorium-226, astatine-211, astatine-217, and uranium-230.

11. A composition useful in targeted radiotherapy of cancer, wherein the composition is of Formula II (II)

[Chemical structure diagram showing a metal complex with M coordinated in a cage structure, flanked by two aromatic rings with A$^1$-A$^{10}$ positions, connected via L$^1$ and L$^2$ linkers]

or a pharmaceutically acceptable salt thereof, wherein
M is an alpha-emitting radionuclide;
A$^1$ is N or CR$^1$;
A$^2$ is N or CR$^2$;
A$^3$ is N or CR$^3$;
A$^4$ is N or CR$^4$;
A$^5$ is N or CR$^5$;
A$^6$ is N or CR$^6$;
A$^7$ is N or CR$^7$;
A$^8$ is N or CR$^8$;
A$^9$ is N or CR$^9$;
A$^{10}$ is N or CR$^{10}$; provided that no more than three of A$^1$, A$^2$, A$^3$, A$^4$, and A$^5$ are N, no more than three of A$^6$, A$^7$, A$^8$, A$^9$, and A$^{10}$ are N, and at least one of A$^1$, A$^2$, A$^3$, A$^4$, A$^5$, A$^6$, A$^7$, A$^8$, A$^9$, and A$^{10}$ is N;
at least one of R$^1$, R$^2$, R$^3$, R$^4$, R$^5$, R$^6$, R$^7$, Ie, R$^9$, and R$^{10}$ is a selective cancer cell targeting group or a selective cancer cell targeting group linked to the carbon atom to which it is attached by a alkylene, —O—, —(OCH$_2$CH$_2$)$_z$— where z is 1, 2, 3, 4, 5, 6, 7, 8, 9, or 10, —S—, —C(O)—, —OC(O)—, —C(O)O—, —C(S)O—, —C(O)NR'—, —C(S)NR'—, —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')—, optionally wherein —O—, —(OCH$_2$CH$_2$)$_z$—, —S—, —C(O)—, —OC(O)—, —C(O)O—, —C(S)O—, —C(O)NR'—, —C(S)NR', —NR' C(O)—, —NR'C(S)—, —NR'—, —NR' C(O)N—, —NR'C(S)N—, —S(O)—, —SO$_2$—, —S(O)$_2$O—, —SO$_2$NR'—, —P(O)(OR')—, —P(O) (R')—, —C(NR')—, —OC(NR')—, —SC(NR')— are each independently linked to the carbon atom to which it is attached by a C$_1$-C$_3$ alkylene;
the remaining R$^1$, R$^2$, R$^3$, R$^4$, R$^5$, R$^6$, R$^7$, R$^8$, R$^9$, and R$^{10}$ are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' where x is 1, 2, 3, 4, 5, 6, 7, 8, 9, or 10, —(OCH$_2$CH$_2$)$_y$—OR' where y is 1, 2, 3, 4, 5, 6, 7, 8, 9, or 10, —SR', —OC(O)R', —C(O)OR', —C(S)OR', —C(O)NR'R', —C(S)NR'R', —NR'C(O)R', —NR'C(S)R', —NR'R', —NR' C(O)NR', —NR' C(S)NR', —S(O)R', —SO$_2$R', —SO$_2$(OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O) OR', —C(S)OR', —C(O)NR'R', —C(S)NR'R', —NR'C(O)R', —NR'C(S)R', —NR'R', —NR'C(O) NR', —NR'C(S)NR', —S(O)R', —SO$_2$(OR'), —SO$_2$NR'$_2$, —P(O)(OR')$_2$, —P(O)R'(OR'), —P(O) R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3;
or one or two pairs of directly adjacent R', R$^2$, R$^3$, R$^4$, R$^5$, R$^6$, R$^7$, R$^8$, R$^9$, and R$^{10}$ groups are interconnected to form a five- to six-membered substituted or unsubstituted carbocyclic or nitrogen-containing ring;
R' is independently at each occurance H, C$_1$-C$_6$ alkyl, C$_3$-C$_6$ cycloalkyl, C$_2$-C$_6$ alkenyl, C$_5$-C$_6$ cycloalkenyl, C$_2$-C$_6$ alkynyl, C$_5$-C$_6$ aryl, heterocyclyl, or heteroaryl, or wherein two R' groups attached to the same atom are interconnected to form a three- to six-membered ring;
L$^1$ and L$^2$ are each independently selected from —(CH$_2$)$_p$—, where p is a value of 1, 2, or 3;
r is 0 or 1; and
s is 0 or 1.

12. The composition of claim 11, wherein said selective cancer cell targeting group contains amino acids linked by peptide bonds.

13. The composition of claim 12, wherein said selective cancer cell targeting group is a cancer-targeting antibody or antibody fragment.

14. The composition of claim 12, wherein said selective cancer cell targeting group is an oligopeptide containing up to 50 amino acids.

15. A method of treating cancer in a subject, the method comprising administering to a subject having cancer an effective amount of a composition of Formula II

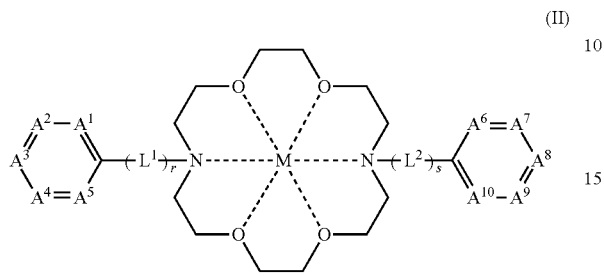

(II)

or a pharmaceutically acceptable salt thereof, wherein:
M is an alpha-emitting radionuclide;
$A^1$ is N or $CR^1$;
$A^2$ is N or $CR^2$;
$A^3$ is N or $CR^3$;
$A^4$ is N or $CR^4$;
$A^5$ is N or $CR^5$;
$A^6$ is N or $CR^6$;
$A^7$ is N or $CR^7$;
$A^8$ is N or $CR^8$;
$A^9$ is N or $CR^9$;
$A^{10}$ is N or $CR^{10}$; provided that no more than three of $A^1$, $A^2$, $A^3$, $A^4$, and $A^5$ are N, no more than three of $A^6$, $A^7$, $A^8$, $A^9$, and $A^{10}$ are N, and at least one of $A^1$, $A^2$, $A^3$, $A^4$, $A^5$, $A^6$, $A^7$, $A^8$, $A^9$, and $A^{10}$ is N;
at least one of $R^1$, $R^2$, $R^3$, $R^4$, $R^5$, $R^6$, $R^7$, $R^8$, $R^9$, and $R^{10}$ is a selective cancer cell targeting group or a selective cancer cell targeting group linked to the carbon atom to which it is attached by a alkylene, —O—, —(OCH$_2$CH$_2$)$_z$ where z is 1, 2, 3, 4, 5, 6, 7, 8, 9, or 10, —S—, —C(O)—, —OC(O)—, —C(O)O—, —C(S)O—, —C(O)NR'—, —C(S)NR', —NR'C(O)—, —NR'C(S)—, —NR'—, —NR'C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')—, optionally wherein —O—, —(OCH$_2$CH$_2$)$_z$—, —S—, —C(O)—, —OC(O)—, —C(O)O—, —C(S)O—, —C(O)NR'—, —C(S)NR', —NR' C(O)—, —NR'C(S)—, —NR'—, —NR' C(O)N—, —NR'C(S)N—, —S(O)—, —SO$_2$—, —S(O)$_2$O—, —SO$_2$NR'—, —P(O)(OR')—, —P(O)(R')—, —C(NR')—, —OC(NR')—, —SC(NR')— are each independently linked to the carbon atom to which it is attached by a $C_1$-$C_3$ alkylene;
the remaining $R^1$, $R^2$, $R^3$, $R^4$, $R^5$, $R^6$, $R^7$, $R^8$, $R^9$, and $R^{10}$ are each independently selected from H, alkyl, cycloalkyl, alkenyl, cycloalkenyl, alkynyl, aryl, heterocyclyl, heteroaryl, halo, —OR', —(OCH$_2$CH$_2$)$_x$—R' (where x is 1, 2, 3, 4, 5, 6, 7, 8, 9, or 10), —(OCH$_2$CH$_2$)$_y$—OR' (where y is 1, 2, 3, 4, 5, 6, 7, 8, 9, or 10), —SR', —OC(O)R', —C(O) OR', —C(S)OR', —C(O)NR'R', —C(S)NR'R', —NR'C(O)R', —NR'C(S)R', —NR'R', —NR'C(O) NR', —NR'C(S)NR', —S(O)R', —SO$_2$R', —SO$_2$ (OR'), —SO$_2$NR'$_2$, —P(O)(OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and an epoxide group, optionally wherein halo, —OR', —(OCH$_2$CH$_2$)$_x$—R', —(OCH$_2$CH$_2$)$_y$—OR', —SR', —OC(O)R', —C(O)OR', —C(S)OR', —C(O)NR'R', —C(S)NR'R', —NR'C(O)R', —NR' C(S)R', —NR'R', —NR' C(O)NR', —NR' C(S)NR', —S(O) R', —SO$_2$R', —SO$_2$(OR'), —SO$_2$NR'$_2$, —P(O) (OR')$_2$, —P(O)R'(OR'), —P(O)R'$_2$, —NO$_2$, —CN, —OCN, —SCN, —NCO, —NCS, —NR'—NR'R', —N, —N=C=N—R', —SO$_2$Cl, —C(O)Cl, and the epoxide group are each independently linked to the carbon atom to which it is attached by a —(CH$_2$)$_n$— linker where n is 1, 2, or 3;
or one or two pairs of directly adjacent $R^1$, $R^2$, $R^3$, $R^4$, $R^5$, $R^6$, $R^7$, $R^8$, $R^9$, and $R^{10}$ groups are interconnected to form a five- to six-membered substituted or unsubstituted carbocyclic or nitrogen-containing ring;
R' is independently at each occurance H, $C_1$-$C_6$ alkyl, $C_3$-$C_6$ cycloalkyl, $C_2$-$C_6$ alkenyl, $C_5$-$C_6$ cycloalkenyl, $C_2$-$C_6$ alkynyl, $C_5$-$C_6$ aryl, heterocyclyl, or heteroaryl, or wherein two R' groups attached to the same atom are interconnected to form a three- to six-membered ring,
$L^1$ and $L^2$ are each independently selected from —(CH$_2$)$_p$—, where p is a value of 1, 2, or 3;
r is 0 or 1; and
s is 0 or 1.

16. The composition of claim 1, wherein the composition is

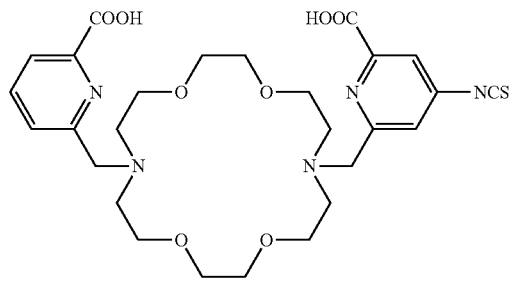

or a pharmaceutically acceptable salt thereof.

* * * * *